US012805845B2

(12) United States Patent
Ebata

(10) Patent No.: US 12,805,845 B2
(45) Date of Patent: Nov. 24, 2026

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Tetsurou Ebata, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/059,185

(22) Filed: Feb. 20, 2025

(65) Prior Publication Data

US 2025/0275757 A1 Sep. 4, 2025

(30) Foreign Application Priority Data

Mar. 4, 2024 (JP) ................................ 2024-031972

(51) Int. Cl.
*A61B 8/00* (2006.01)

(52) U.S. Cl.
CPC ............ *A61B 8/523* (2013.01); *A61B 8/4254* (2013.01); *A61B 8/463* (2013.01); *A61B 8/466* (2013.01); *A61B 8/5238* (2013.01)

(58) Field of Classification Search
CPC ......... A61B 8/483; A61B 8/466; A61B 8/463; A61B 8/4254; A61B 8/5238
See application file for complete search history.

(56) References Cited

U.S. PATENT DOCUMENTS

| | | | | |
|---|---|---|---|---|
| 2015/0178921 | A1 | 6/2015 | Hashimoto et al. | |
| 2025/0132030 | A1* | 4/2025 | Ishikawa | G16H 30/40 |
| 2025/0272844 | A1* | 8/2025 | Shim | G06N 3/045 |

FOREIGN PATENT DOCUMENTS

| | | |
|---|---|---|
| JP | 2012-055765 A | 3/2012 |
| JP | 2014-061291 A | 4/2014 |

(Continued)

OTHER PUBLICATIONS

Extended European Search Report issued in EP 25 15 9971.8-1122 by the European Patent Office on Jul. 24, 2025, which is related to U.S. Appl. No. 19/059,185.

*Primary Examiner* — Gerald Johnson
(74) *Attorney, Agent, or Firm* — Studebaker Brackett PLLC

(57) ABSTRACT

Provided are an ultrasound diagnostic apparatus that enables a user to easily visualize an appropriate cross section of an organ as an examination target regardless of a skill level, and a method of controlling an ultrasound diagnostic apparatus. An ultrasound diagnostic apparatus includes a three-dimensional ultrasound image acquisition unit that acquires a three-dimensional ultrasound image by transmitting and receiving an ultrasound beam by using an ultrasound probe, an arbitrary cross section image generation unit that cuts out an arbitrary cross section image from the three-dimensional ultrasound image, a cross section determination unit that compares an image pattern of a recommended cross section with an image pattern of the arbitrary cross section image, to determine whether or not the arbitrary cross section image represents the recommended cross section, and a scanning guide unit that guides scanning toward a target position and a target posture angle of the ultrasound probe for imaging the recommended cross section with reference to the position and the posture angle of the ultrasound probe, which are detected, in a case in which it is determined that the arbitrary cross section image represents the recommended cross section.

20 Claims, 14 Drawing Sheets

(56) References Cited

FOREIGN PATENT DOCUMENTS

| | | | | | |
|---|---|---|---|---|---|
| JP | 2018-051346 | A | | 4/2018 | |
| WO | WO-2020246894 | A1 | * | 12/2020 | ............... A61B 8/10 |

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

The present application claims priority under 35 U.S.C. § 119 to Japanese Patent Application No. 2024-031972, filed on Mar. 4, 2024. The above application is hereby expressly incorporated by reference, in its entirety, into the present application.

BACKGROUND OF THE INVENTION

1. Field of the Invention

The present invention relates to an ultrasound diagnostic apparatus that guides a user to perform scanning with an ultrasound probe, and a method of controlling an ultrasound diagnostic apparatus.

2. Description of the Related Art

In the related art, an ultrasound image representing a tomogram of a subject is captured by using a so-called ultrasound diagnostic apparatus, thereby examining an inside of the subject. In this case, a user of the ultrasound diagnostic apparatus usually moves an ultrasound probe to a position on the subject at which a target part can be imaged while checking the captured ultrasound image, but it may be difficult for the user who has a low skill level of an examination using the ultrasound diagnostic apparatus to determine which part of the subject is imaged even in a case in which the ultrasound image is checked.

Therefore, for example, as disclosed in JP2014-061291A, a technology has been developed in which a medical image obtained by a modality other than an ultrasound diagnostic apparatus, such as a computed tomography (CT) image or a magnetic resonance imaging (MRI) image, which is stored in advance and corresponds to a tomogram in a subject represented by an ultrasound image during imaging, is displayed as a reference image, so that a user can easily understand which part is currently being imaged.

SUMMARY OF THE INVENTION

Since a shape, a size, a disposition position, and the like of an organ are different for each subject, a position and an angle of an appropriate cross section that clearly shows the organ to be examined may also be different for each subject. Therefore, for example, even in a case in which the technology of JP2014-061291A is used, in particular, in a case in which a user who has a low skill level of the examination using the ultrasound diagnostic apparatus performs the examination, it takes a long time to visualize an appropriate cross section of the organ in the ultrasound image, or it is difficult to visualize an appropriate cross section of the organ in the first place.

The present invention has been made in order to solve such a problem in the related art, and an object of the present invention is to provide an ultrasound diagnostic apparatus that enables a user to easily visualize an appropriate cross section of an organ as an examination target regardless of a skill level, and a method of controlling an ultrasound diagnostic apparatus.

With the following configuration, the above-described object can be achieved.

[1] An ultrasound diagnostic apparatus comprising: an ultrasound probe; a position/posture detection unit that detects a position and a posture angle of the ultrasound probe; a three-dimensional ultrasound image acquisition unit that acquires a three-dimensional ultrasound image of an inside of a subject by transmitting and receiving an ultrasound beam by using the ultrasound probe with reference to the position and the posture angle of the ultrasound probe, which are detected by the position/posture detection unit; an arbitrary cross section image generation unit that cuts out a two-dimensional arbitrary cross section image from the three-dimensional ultrasound image acquired by the three-dimensional ultrasound image acquisition unit, to generate the arbitrary cross section image; a cross section determination unit that compares an image pattern of a predetermined recommended cross section for a part of the subject with an image pattern of the arbitrary cross section image generated by the arbitrary cross section image generation unit, to determine whether or not the arbitrary cross section image represents the recommended cross section; and a scanning guide unit that guides a user to perform scanning with the ultrasound probe toward a target position and a target posture angle of the ultrasound probe for capturing a two-dimensional ultrasound image representing the recommended cross section with reference to the position and the posture angle of the ultrasound probe, which are detected by the position/posture detection unit, in a case in which the cross section determination unit determines that the arbitrary cross section image represents the recommended cross section.

[2] The ultrasound diagnostic apparatus according to [1], in which the cross section determination unit calculates a matching degree between the image pattern of the recommended cross section and the image pattern of the arbitrary cross section image generated by the arbitrary cross section image generation unit, and determines that the arbitrary cross section image of which the matching degree exceeds a predetermined threshold value represents the recommended cross section.

[3] The ultrasound diagnostic apparatus according to [1] or [2], further comprising: an image memory that stores the arbitrary cross section image determined to represent the recommended cross section by the cross section determination unit.

[4] The ultrasound diagnostic apparatus according to [3], further comprising: an image quality determination unit that determines whether or not a quality of the arbitrary cross section image determined to represent the recommended cross section by the cross section determination unit is superior, in which the image memory stores the arbitrary cross section image for which the image quality determination unit determines that the quality is superior.

[5] The ultrasound diagnostic apparatus according to any one of [1] to [4], further comprising: a scanning prompt unit that prompts the user to perform the scanning with the ultrasound probe in a case in which the cross section determination unit does not determine that the arbitrary cross section image represents the recommended cross section even after a predetermined time has elapsed since a start of the scanning with the ultrasound probe.

[6] The ultrasound diagnostic apparatus according to any one of [1] to [5], further comprising: a monitor, in which the scanning guide unit displays, on the monitor, a schema image in which the target position and the target posture angle of the ultrasound probe and a current position and a current posture angle of the ultrasound probe are superimposed.

[7] The ultrasound diagnostic apparatus according to any one of [1] to [6], in which the cross section determination unit stores a plurality of different recommended cross sections, and the ultrasound diagnostic apparatus further comprises: a cross section specification information display unit that displays, on a monitor, cross section specification information for specifying the recommended cross section determined to be represented by the arbitrary cross section image by the cross section determination unit among the plurality of different recommended cross sections.

[8] The ultrasound diagnostic apparatus according to [1] to [6], in which the cross section determination unit stores a plurality of different recommended cross sections, and sets the recommended cross section that has been imaged among the plurality of different recommended cross sections, as a target not to be determined.

[9] The ultrasound diagnostic apparatus according to any one of [1] to [6], in which the cross section determination unit stores a plurality of different recommended cross sections and a target position and a target posture angle for imaging each of the plurality of different recommended cross sections, and the scanning guide unit guides the user to perform the scanning with the ultrasound probe toward the target position and the target posture angle of the ultrasound probe, which correspond to the recommended cross section that has not yet been imaged, in a case in which the cross section determination unit determines that the arbitrary cross section image represents the recommended cross section that has been imaged among the plurality of different recommended cross sections.

[10] The ultrasound diagnostic apparatus according to any one of [1] to [6], in which the cross section determination unit stores a plurality of different recommended cross sections, an indicator cross section different from the plurality of different recommended cross sections, and a correspondence relationship between target positions and target posture angles of the ultrasound probe for imaging the plurality of different recommended cross sections and a position and a posture angle of the ultrasound probe for imaging the indicator cross section, and calculates a matching degree between image patterns of the plurality of different recommended cross sections and the image pattern of the arbitrary cross section image generated by the arbitrary cross section image generation unit and a matching degree between an image pattern of the indicator cross section and the image pattern of the arbitrary cross section image generated by the arbitrary cross section image generation unit, and the scanning guide unit guides, in a case in which the matching degree between the image pattern of the indicator cross section and the image pattern of the arbitrary cross section image exceeds a predetermined threshold value, the user to perform the scanning with the ultrasound probe toward a position and a posture angle of the ultrasound probe for capturing a two-dimensional ultrasound image representing the indicator cross section, and then guides the user to perform the scanning with the ultrasound probe toward the target position and the target posture angle corresponding to any one of the plurality of different recommended cross sections based on the correspondence relationship.

[11] The ultrasound diagnostic apparatus according to any one of [1] to [10], in which the arbitrary cross section image generation unit cuts out a plurality of first arbitrary cross section images from the three-dimensional ultrasound image acquired by the three-dimensional ultrasound image generation unit, at a predetermined first positional interval and a predetermined first angular interval, to generate the plurality of first arbitrary cross section images, the cross section determination unit calculates a first matching degree between the image pattern of the recommended cross section and image patterns of the plurality of first arbitrary cross section images, and determines whether or not the first matching degree is greater than a predetermined first threshold value and equal to or less than a predetermined second threshold value, the arbitrary cross section image generation unit cuts out a plurality of second arbitrary cross section images from a partial region of the three-dimensional ultrasound image including the first arbitrary cross section image corresponding to the first matching degree, at a second positional interval smaller than the first positional interval and a second angular interval smaller than the first angular interval, to generate the plurality of second arbitrary cross section images in a case in which the cross section determination unit determines that the first matching degree is greater than the first threshold value and equal to or less than the second threshold value, the cross section determination unit compares the image pattern of the recommended cross section with image patterns of the plurality of second arbitrary cross section images, to determine whether or not any one of the plurality of second arbitrary cross section images represents the recommended cross section, and the scanning guide unit guides the user to perform the scanning with the ultrasound probe toward the target position and the target posture angle of the ultrasound probe for capturing the two-dimensional ultrasound image representing the recommended cross section in a case in which the cross section determination unit determines that any one of the plurality of second arbitrary cross section images represents the recommended cross section.

[12] A method of controlling an ultrasound diagnostic apparatus, the method comprising: detecting a position and a posture angle of an ultrasound probe; generating a plurality of two-dimensional ultrasound images of an inside of a subject by transmitting and receiving an ultrasound beam by using the ultrasound probe with reference to the position and the posture angle of the ultrasound probe, which are detected; generating a three-dimensional ultrasound image of the inside of the subject based on the position and the posture angle of the ultrasound probe, which are detected, and the plurality of two-dimensional ultrasound images; cutting out a two-dimensional arbitrary cross section image from the three-dimensional ultrasound image, to generate the arbitrary cross section image; comparing an image pattern of a predetermined recommended cross section for a part of the subject with an image pattern of the arbitrary cross section image, to determine whether or not the arbitrary cross section image represents the recommended cross section; and guiding a user to perform scanning with the ultrasound probe toward a target position and a target posture angle of the ultrasound probe for capturing a two-dimensional ultrasound image representing the recommended cross section in a case in which it is determined that the arbitrary cross section image represents the recommended cross section.

The aspect of the present invention relates to the ultrasound diagnostic apparatus comprising: the ultrasound probe; the position/posture detection unit that detects the position and the posture angle of the ultrasound probe; the three-dimensional ultrasound image acquisition unit that acquires the three-dimensional ultrasound image of the inside of the subject by transmitting and receiving the ultrasound beam by using the ultrasound probe with reference to the position and the posture angle of the ultrasound probe, which are detected by the position/posture detection unit; the arbitrary cross section image generation unit that cuts out the two-dimensional arbitrary cross section image from the three-dimensional ultrasound image acquired by the three-dimensional ultrasound image acquisition unit, to generate the arbitrary cross section image; the cross section determination unit that compares the image pattern of the predetermined recommended cross section for the part of the subject with the image pattern of the arbitrary cross section image generated by the arbitrary cross section image generation unit, to determine whether or not the arbitrary cross section image represents the recommended cross section; and the scanning guide unit that guides the user to perform the scanning with the ultrasound probe toward the target position and the target posture angle of the ultrasound probe for capturing the two-dimensional ultrasound image representing the recommended cross section with reference to the position and the posture angle of the ultrasound probe, which are detected by the position/posture detection unit, in a case in which the cross section determination unit determines that the arbitrary cross section image represents the recommended cross section, so that it is possible for the user to easily visualize an appropriate cross section of the organ as the examination target, regardless of the skill level.

DESCRIPTION OF THE PREFERRED EMBODIMENTS

Hereinafter, embodiments of the present invention will be described based on the accompanying drawings.

The configuration requirements are described later based on a representative embodiment of the present invention, but the present invention is not limited to such an embodiment.

In the present specification, a numerical range represented by "to" means a range including numerical values described before and after "to" as a lower limit value and an upper limit value.

In the present specification, "the same" includes an error range generally allowed in the technical field.

Embodiment 1

Figure 1:
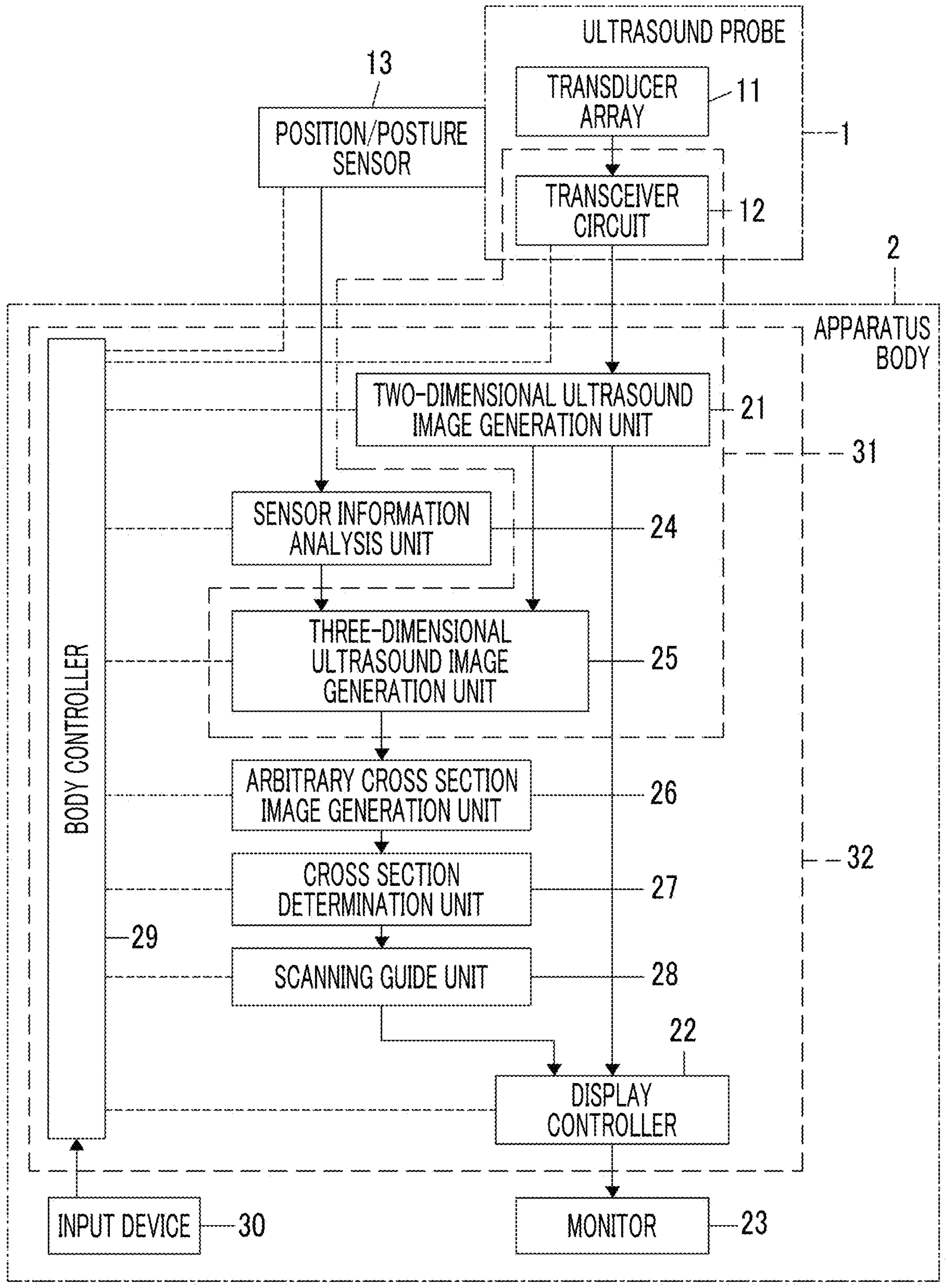
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1, and an apparatus body 2 connected to the ultrasound probe 1. The ultrasound probe 1 and the apparatus body 2 are connected to each other via so-called wired communication or so-called wireless communication.

The ultrasound probe 1 includes a transducer array 11. A transceiver circuit 12 is connected to the transducer array 11. The ultrasound probe 1 includes a position/posture sensor 13. The position/posture sensor 13 may be incorporated in the ultrasound probe 1 or attached to a housing of the ultrasound probe 1. In addition, in a case in which a sensor device that measures the ultrasound probe 1 from the outside, such as a so-called optical sensor, is used as the position/posture sensor 13, the position/posture sensor 13 may be disposed at a position away from the ultrasound probe 1.

The apparatus body 2 includes a two-dimensional ultrasound image generation unit 21 connected to the transceiver circuit 12 of the ultrasound probe 1. A display controller 22 and a monitor 23 are connected in order to the two-dimensional ultrasound image generation unit 21. In addition, the apparatus body 2 includes a sensor information analysis unit 24 that is connected to the position/posture sensor 13 of the ultrasound probe 1. A three-dimensional ultrasound image generation unit 25 is connected to the two-dimensional ultrasound image generation unit 21 and the sensor information analysis unit 24. A three-dimensional ultrasound image generation unit 25 is connected in order to an arbitrary cross section image generation unit 26, a cross section determination unit 27, and a scanning guide unit 28. The scanning guide unit 28 is connected to the display controller 22. In addition, a body controller 29 is connected to the transceiver circuit 12, the position/posture sensor 13, the two-dimensional ultrasound image generation unit 21, the display controller 22, the sensor information analysis unit 24, the three-dimensional ultrasound image generation unit 25, the arbitrary cross section image generation unit 26, the cross section determination unit 27, and the scanning guide unit 28. An input device 30 is connected to the body controller 29.

The transceiver circuit 12, the two-dimensional ultrasound image generation unit 21, and the three-dimensional ultrasound image generation unit 25 constitute a three-dimensional ultrasound image acquisition unit 31. In addition, the two-dimensional ultrasound image generation unit 21, the display controller 22, the sensor information analysis unit 24, the three-dimensional ultrasound image generation unit 25, the arbitrary cross section image generation unit 26, the cross section determination unit 27, the scanning guide unit 28, and the body controller 29 constitute a processor 32 for the apparatus body 2.

The transducer array 11 of the ultrasound probe 1 includes a plurality of ultrasound transducers arranged one-dimensionally or two-dimensionally. In response to a drive signal supplied from the transceiver circuit 12, each of the ultrasound transducers transmits ultrasound and receives an ultrasound echo from a subject to output a signal based on the ultrasound echo. For example, each ultrasound transducer is configured by forming electrodes at both ends of a piezoelectric material consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), and the like.

As will be described later, the three-dimensional ultrasound image acquisition unit 31 configured by the transceiver circuit 12, the two-dimensional ultrasound image generation unit 21, and the three-dimensional ultrasound image generation unit 25 acquires a three-dimensional ultrasound image of an inside of the subject by transmitting and receiving an ultrasound beam by using the ultrasound probe 1 with reference to the position and the posture angle of the ultrasound probe 1 detected by the position/posture sensor 13 and the sensor information analysis unit 24.

Figure 2:
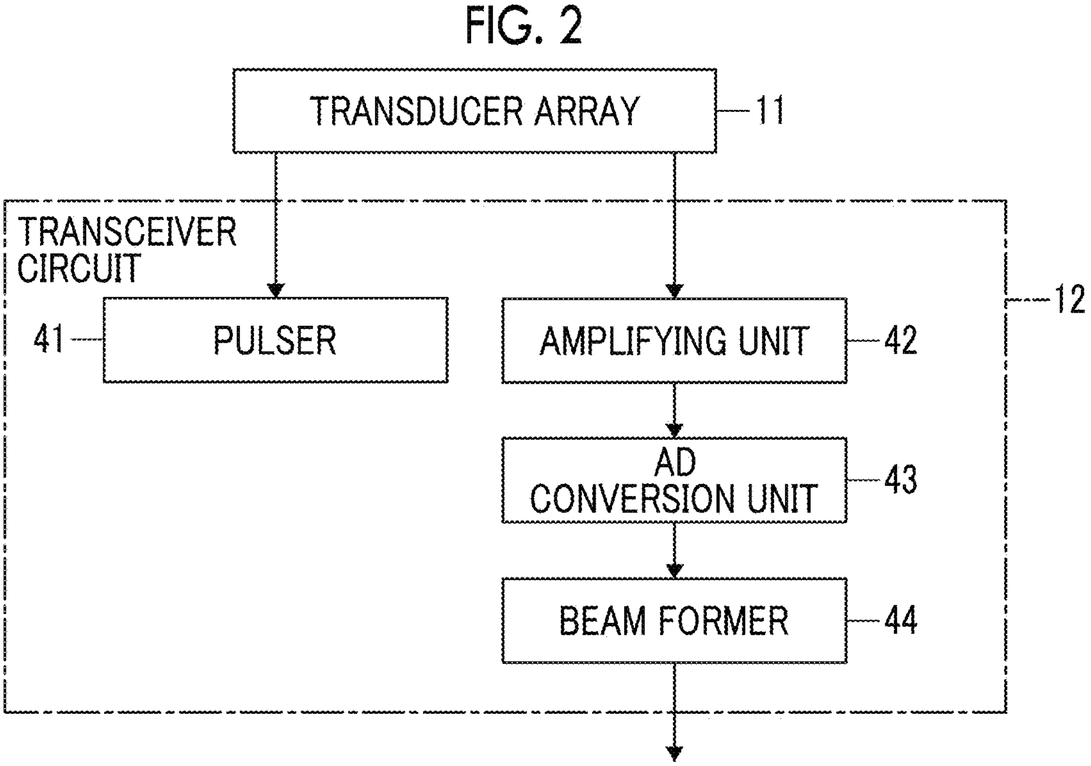
FIG. 2 is a block diagram showing a configuration of a transceiver circuit according to Embodiment 1 of the present invention.

Under the control of the body controller 29, the transceiver circuit 12 causes the transducer array 11 to transmit the ultrasound and generates a sound ray signal based on a reception signal acquired by the transducer array 11. As shown in FIG. 2, the transceiver circuit 12 includes a pulser 41 connected to the transducer array 11, and an amplifying unit 42, an analog-to-digital (AD) conversion unit 43, and a beam former 44 that are sequentially connected in series to the transducer array 11.

The pulser 41 includes, for example, a plurality of pulse generators, and the pulser 41 adjusts an amount of delay of each drive signal such that the ultrasound transmitted from the plurality of ultrasound transducers of the transducer array 11 form the ultrasound beam, based on a transmission delay pattern selected in accordance with a control signal from the body controller 29, and supplies the adjusted signal to the plurality of ultrasound transducers. In this way, in a case in which a pulsed or continuous wave-like voltage is applied to the electrodes of the ultrasound transducer of the transducer array 11, the piezoelectric material expands and contracts to generate pulsed or continuous wave-like ultrasound from each of the ultrasound transducers, whereby the ultrasound beam is formed from the combined wave of the ultrasound.

The transmitted ultrasound beam is, for example, reflected in a target such as a part of the subject and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate the reception signal, which is an electrical signal, and outputs these reception signals to the amplifying unit 42.

The amplifying unit 42 amplifies the signal input from each of the ultrasound transducers constituting the transducer array 11 and transmits the amplified signal to the AD conversion unit 43. The AD conversion unit 43 converts the signal transmitted from the amplifying unit 42 into digital reception data. The beam former 44 performs so-called reception focus processing by applying and adding the delay to each reception data received from the AD conversion unit 43. By this reception focus processing, each reception data converted by the AD conversion unit 43 is phase-added, and the sound ray signal in which the focus of the ultrasound echo is narrowed down is acquired.

Figure 3:
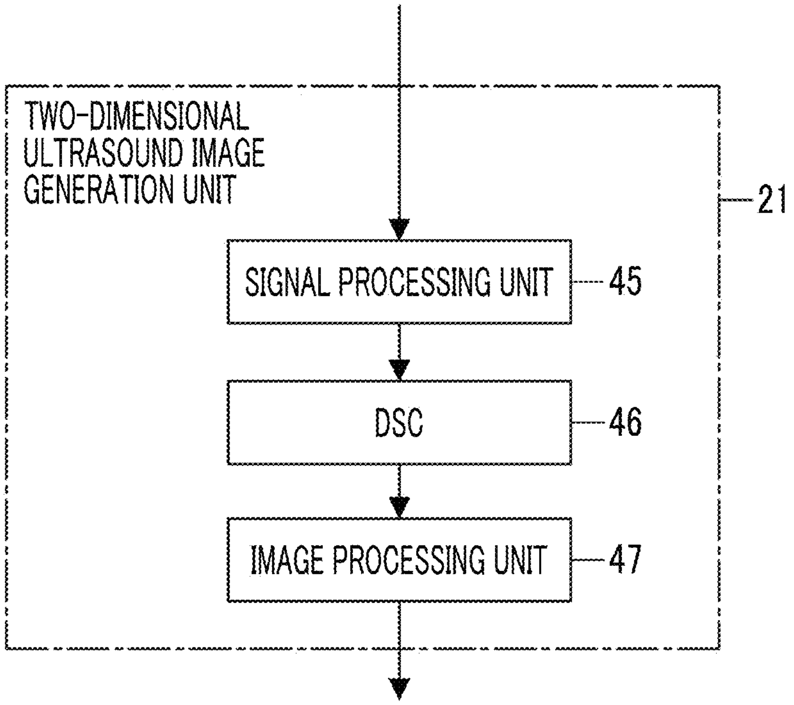
FIG. 3 is a block diagram showing a configuration of a two-dimensional ultrasound image generation unit according to Embodiment 1 of the present invention.

As shown in FIG. 3, the two-dimensional ultrasound image generation unit 21 has a configuration in which a signal processing unit 45, a digital scan converter (DSC) 46, and an image processing unit 47 are sequentially connected in series to each other.

The signal processing unit 45 generates a B-mode image signal, which is tomographic image information related to tissues inside the subject, by performing, on the sound ray signal received from the transceiver circuit 12, correction of the attenuation due to a distance in accordance with a depth of a reflection position of the ultrasound by using a sound velocity value set by the body controller 29 and then performing envelope detection processing.

The DSC 46 converts (raster-converts) the B-mode image signal generated by the signal processing unit 45 into the image signal in accordance with a normal television signal scanning method.

The image processing unit 47 performs various types of necessary image processing such as gradation processing on the B-mode image signal input from the DSC 46, and then sends the B-mode image signal to the display controller 22 and the three-dimensional ultrasound image generation unit 25. Hereinafter, the B-mode image signal that is image-processed by the image processing unit 47 will be referred to as a two-dimensional ultrasound image.

The position/posture sensor 13 is a sensor device that acquires a signal representing the position and the posture angle of the ultrasound probe 1 under the control of the body controller 29. The position of the ultrasound probe 1 represents a position of the ultrasound probe 1 in a three-dimensional space. The posture angle of the ultrasound probe 1 represents an inclined angle and a rotation angle of the ultrasound probe 1 in the three-dimensional space. The position/posture sensor 13 can include, for example, at least one of a so-called inertial sensor, a magnetic sensor, an optical sensor, or an optical camera. The inertial sensor can include, for example, at least one of a so-called acceleration sensor or a gyro sensor.

The sensor information analysis unit 24 analyzes the signal transmitted from the position/posture sensor 13 to acquire information representing the position and the posture angle of the ultrasound probe 1. The sensor information analysis unit 24 can acquire the information representing the position and the posture angle of the ultrasound probe 1 by using, for example, a trained model in so-called machine learning, which has learned a large amount of information on a relationship between the signal obtained by the sensor device constituting the position/posture sensor 13 and the position and the posture angle of the ultrasound probe 1. The sensor information analysis unit 24 can acquire, for example, coordinate values of three components along three axes orthogonal to each other in a rectangular coordinate system as the information representing the position of the ultrasound probe 1. Further, the sensor information analysis unit 24 can acquire, for example, a so-called Euler angle defined in a rectangular coordinate system as the information representing the posture angle of the ultrasound probe 1.

The three-dimensional ultrasound image generation unit 25 generates a three-dimensional ultrasound image representing a part of an organ in the subject based on the information on the position and the posture angle of the ultrasound probe 1 acquired by the sensor information analysis unit 24 and a plurality of two-dimensional ultrasound images generated by the two-dimensional ultrasound image generation unit 21. The three-dimensional ultrasound image generation unit 25 can generate the three-dimensional ultrasound image by arranging the plurality of two-dimensional ultrasound images in the three-dimensional space in accordance with, for example, the information on the position and the posture angle of the ultrasound probe 1 obtained in a state in which the user moves the ultrasound probe 1 on the subject. In this case, the three-dimensional ultrasound image generation unit 25 can also perform processing of interpolating between the plurality of two-dimensional ultrasound images arranged in the three-dimensional space by using, for example, a known algorithm such as so-called nearest neighbor interpolation, linear interpolation, or polynomial interpolation.

It should be noted that the three-dimensional ultrasound image generation unit 25 can sequentially perform processing of generating the three-dimensional ultrasound image each time the ultrasound image is generated by the two-dimensional ultrasound image generation unit 21. Further, the three-dimensional ultrasound image generation unit 25 can also perform processing of generating the three-dimensional ultrasound image at a timing at which a certain number of ultrasound images are acquired.

The arbitrary cross section image generation unit 26 cuts out a two-dimensional arbitrary cross section image from the three-dimensional ultrasound image generated by the three-dimensional ultrasound image generation unit 25, to generate the two-dimensional arbitrary cross section image. In this case, the arbitrary cross section image generation unit 26 can cut out an arbitrary cross section image A by defining a direction perpendicular to the body surface of the subject as a Z direction, a direction orthogonal to the Z direction as an X direction, and a direction orthogonal to the X direction and the Z direction as a Y direction and by using at least one of a method of cutting out the arbitrary cross section image A along a YZ plane while changing the cutout position along the X direction in a three-dimensional ultrasound image T, for example, as shown in FIG. 4, a method of cutting out the arbitrary cross section image A along an XZ plane while changing the cutout position along the Y direction as shown in FIG. 5, a method of cutting out the arbitrary cross section image Awhile changing a rotation angle about a rotation axis extending along the Z direction as shown in FIG. 6, or a method of cutting out the arbitrary cross section image Awhile changing a rotation angle about a rotation axis extending along an XY plane as shown in FIG. 7, or by combining these plurality of methods.

Figure 4:
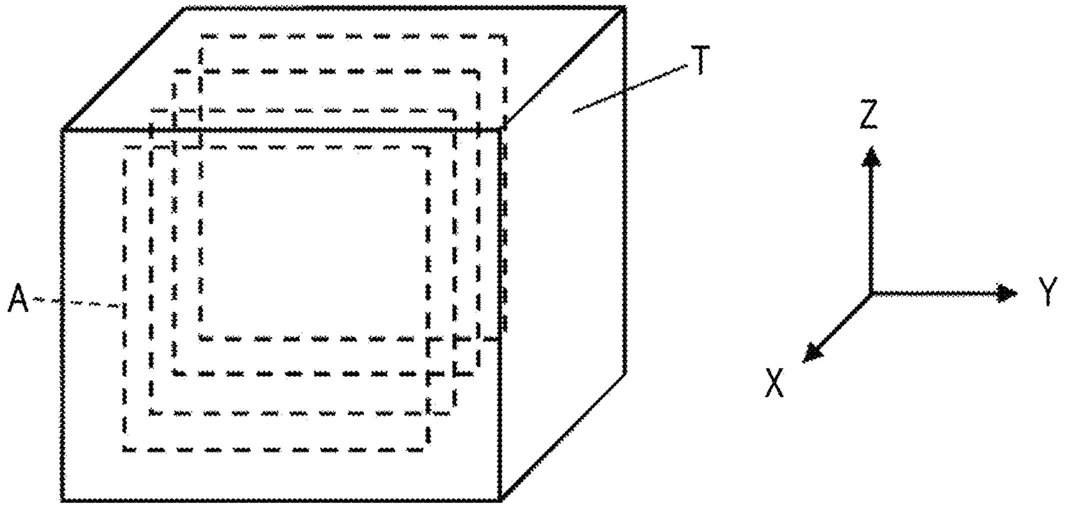
FIG. 4 is a diagram showing a first example of a method of cutting out an arbitrary cross section image.
Figure 5:
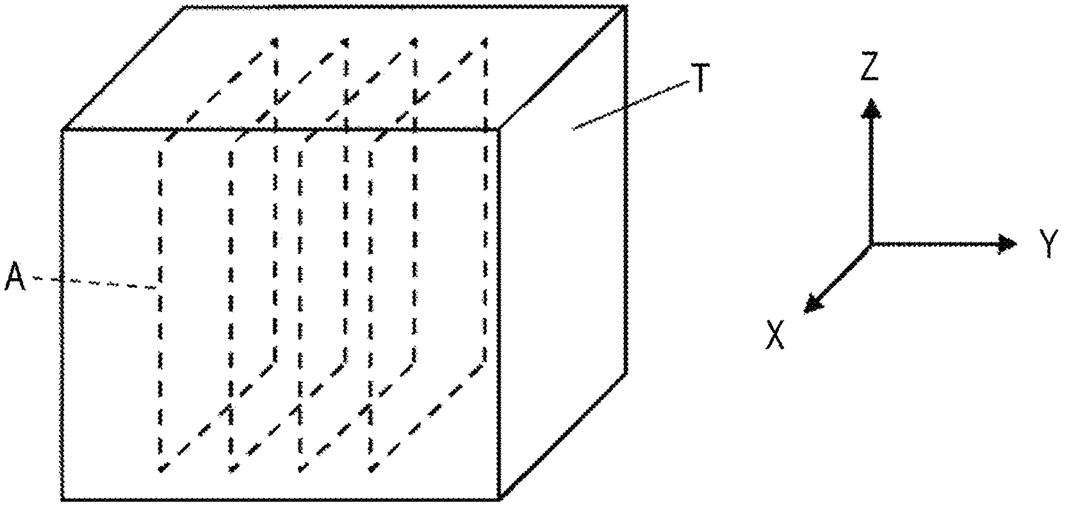
FIG. 5 is a diagram showing a second example of the method of cutting out the arbitrary cross section image.
Figure 6:
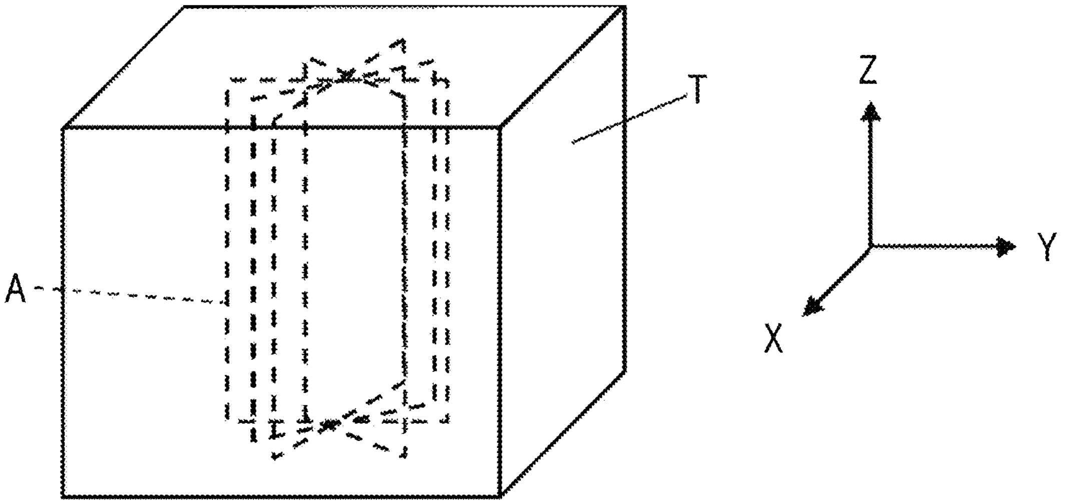
FIG. 6 is a diagram showing a third example of the method of cutting out the arbitrary cross section image.
Figure 7:
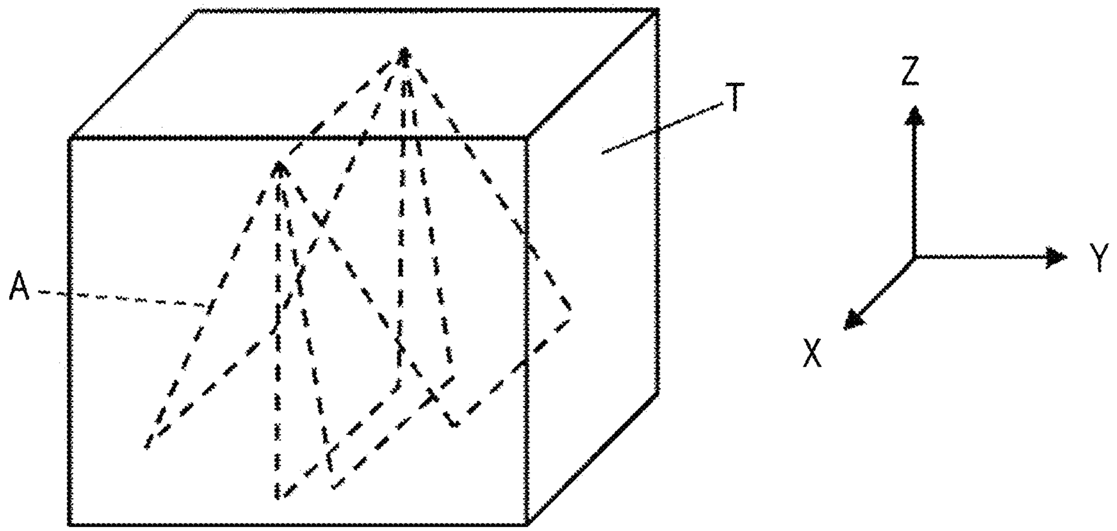
FIG. 7 is a diagram showing a fourth example of the method of cutting out the arbitrary cross section image.

The arbitrary cross section image generation unit 26 can cut out, for example, about five arbitrary cross section images every 1 cm in the X direction in a case in which a plurality of arbitrary cross section images A are cut out as in FIG. 4, can cut out, for example, about five arbitrary cross section images A every 1 cm in the Y direction in a case in which the plurality of arbitrary cross section images A are cut out as in FIG. 5, can cut out, for example, about 10 arbitrary cross section images Aby rotating the arbitrary cross section image by about 18 degrees around a rotation axis extending along the Z direction in a case in which the plurality of arbitrary cross section images A are cut out as in FIG. 6, and can cut out, for example, about 10 arbitrary cross section images A by rotating the arbitrary cross section image by about 18 degrees around a rotation axis extending along the XY plane in a case in which the plurality of arbitrary cross section images A are cut out as in FIG. 7. The arbitrary cross section image generation unit 26 can generate a large number of arbitrary cross section images A by combining these methods.

The arbitrary cross section image generation unit 26 calculates information on the imaging position and the posture angle of the ultrasound probe 1 corresponding to the cutout arbitrary cross section image A based on the imaging positions of the plurality of ultrasound images used in generating the three-dimensional ultrasound image T and the information on the posture angle of the ultrasound probe 1 at the imaging positions, and associates the calculated information with the arbitrary cross section image A.

The cross section determination unit 27 compares an image pattern of the predetermined recommended cross section for the part of the subject with an image pattern of the arbitrary cross section image A generated by the arbitrary cross section image generation unit 26, to determine whether or not the arbitrary cross section image A represents the recommended cross section. Here, the recommended cross section is a cross section in which the examination is recommended for a predetermined part of a specific subject. This recommended cross section can be determined, for example, for each hospital, for each subject, or for each user, or can be determined in accordance with a manual determined by a specialized academic society or the like.

The cross section determination unit 27 can calculate a matching degree between the image pattern of the arbitrary cross section image A and the image pattern of the recommended cross section by using, for example, a trained model in machine learning, which has learned a relationship between the image patterns of a large number of arbitrary cross section images A and the image pattern of the recommended cross section, and determine that the arbitrary cross section image A of which the matching degree exceeds a predetermined threshold value represents the recommended cross section. In addition, the cross section determination unit 27 can also store the image pattern of the recommended cross section in advance and calculate the matching degree between the image pattern of the arbitrary cross section image A and the image pattern of the recommended cross section by performing the image analysis. The cross section determination unit 27 can use, for example, a so-called template matching method in which the image pattern of the recommended cross section is used as a template as the image analysis.

In addition, the cross section determination unit 27 can input the arbitrary cross section image A to a trained model in machine learning, which has learned the relationship between the image patterns of a large number of the arbitrary cross section images A and the image pattern of the recommended cross section, and output a determination result of whether or not the input arbitrary cross section image A represents the recommended cross section to the trained model.

Figure 8:
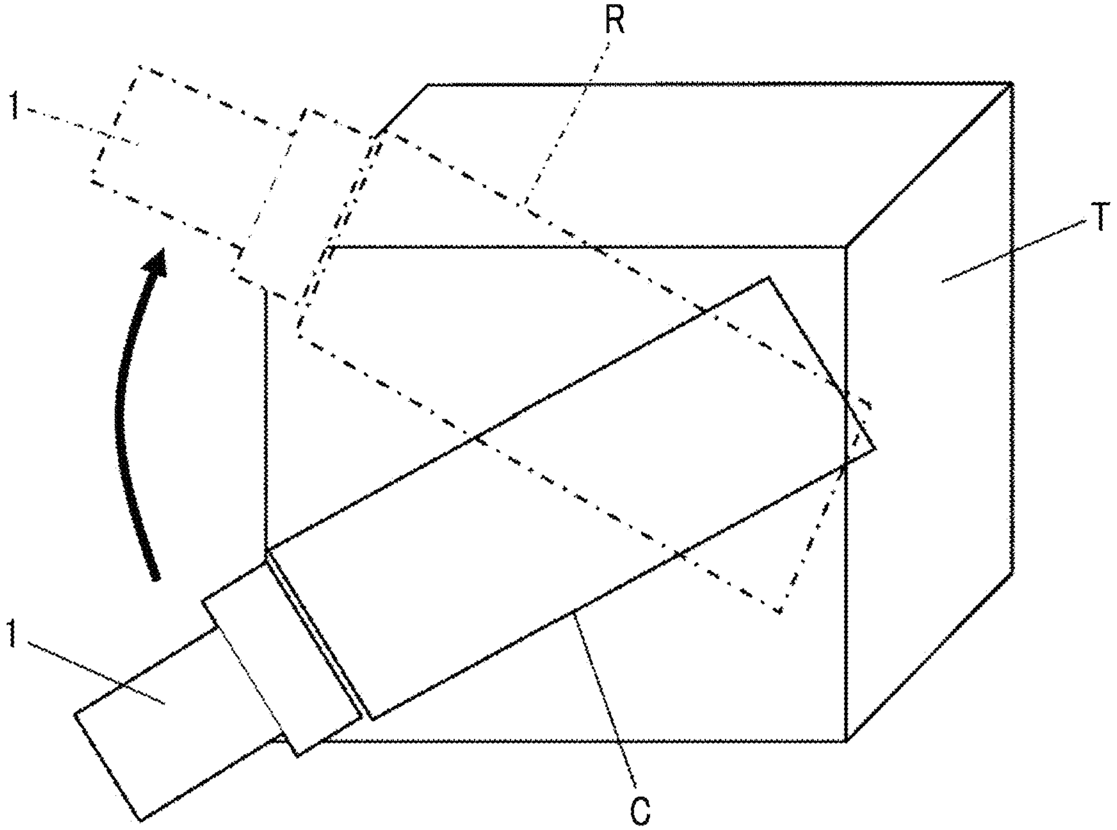
FIG. 8 is a schematic diagram showing an example of a cross section currently being imaged and a recommended cross section.

In a case in which the cross section determination unit 27 determines that the arbitrary cross section image A represents the recommended cross section, the scanning guide unit 28 guides the user to perform the scanning with the ultrasound probe 1 from the position and the posture angle of the ultrasound probe 1 capturing the two-dimensional ultrasound image representing a current cross section C toward a target position and a target posture angle of the ultrasound probe 1 for capturing the two-dimensional ultrasound image representing a recommended cross section R included in the three-dimensional ultrasound image T with reference to the information representing the position and the posture angle of the ultrasound probe 1 acquired by the sensor information analysis unit 24, as schematically shown in FIG. 8.

Figure 9:
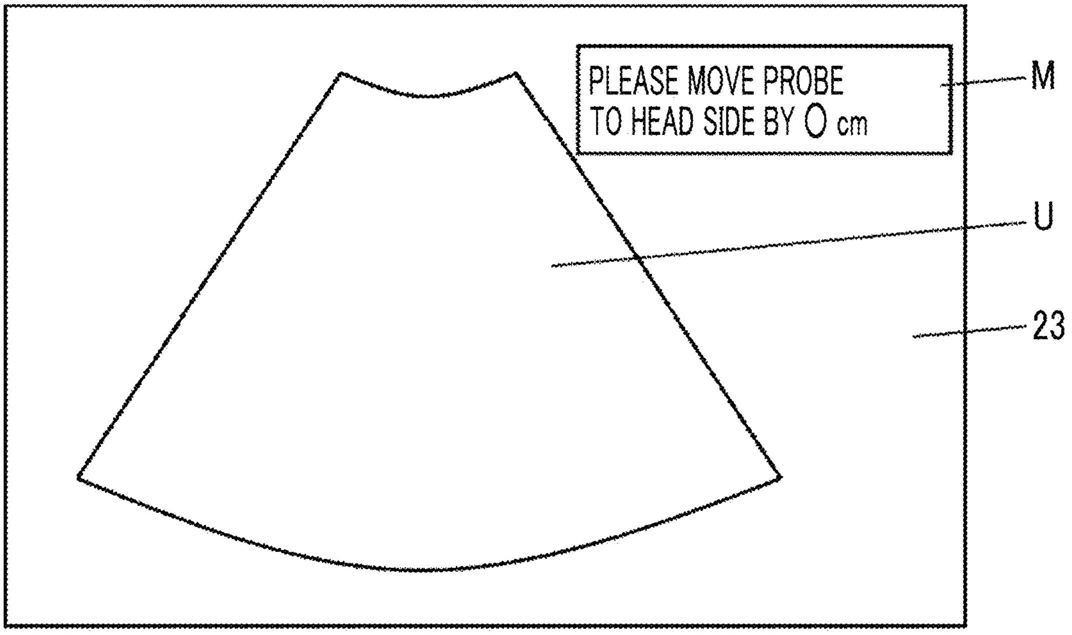
FIG. 9 is a diagram showing a first example of a message for guiding scanning with an ultrasound probe.
Figure 10:
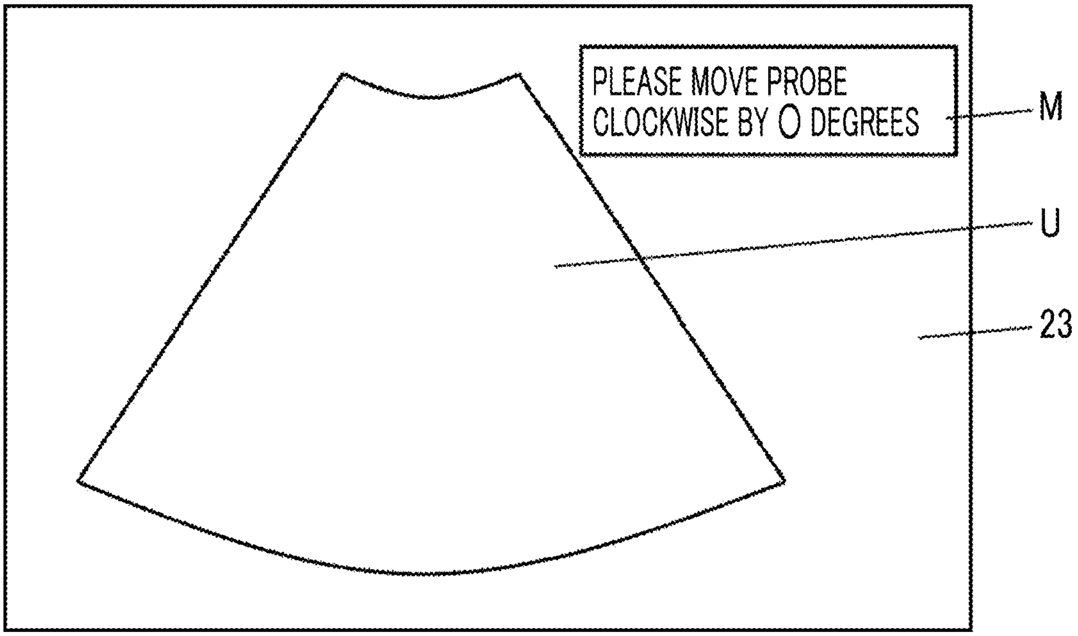
FIG. 10 is a diagram showing a second example of a message for guiding the scanning with the ultrasound probe.
Figure 11:
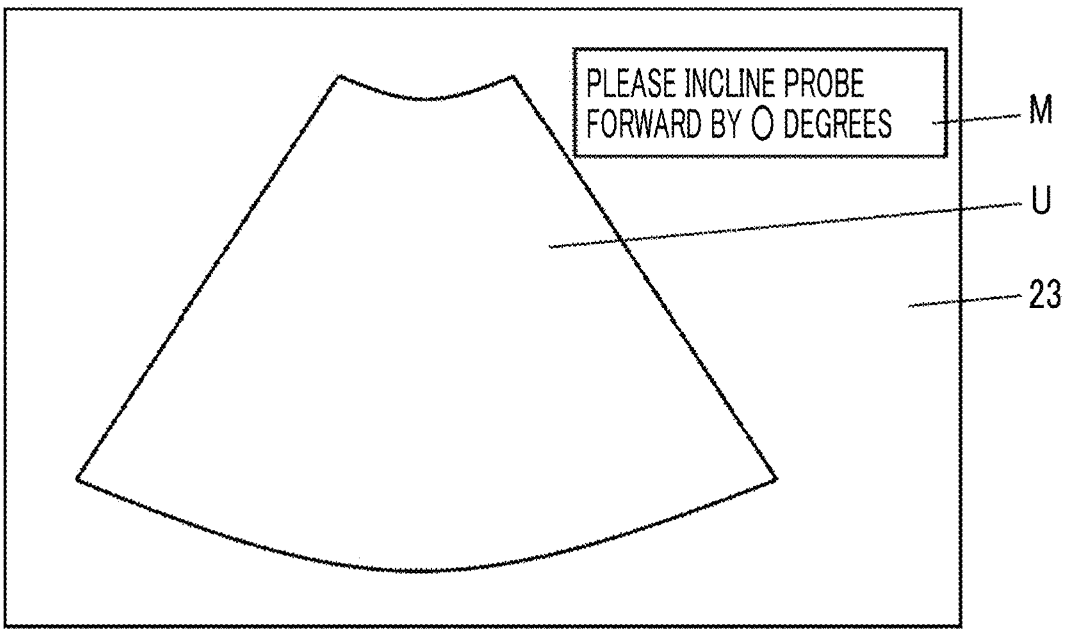
FIG. 11 is a diagram showing a third example of a message for guiding the scanning with the ultrasound probe.

For example, as shown in FIGS. 9 to 11, the scanning guide unit 28 can guide the user to perform the scanning with the ultrasound probe 1 by displaying a message M, such as "Please move the probe by ○ cm toward the head side", "Please move the probe by ○ degrees in the clockwise direction", and "Please incline the probe by ○ degrees forward", on the monitor 23. In the examples of FIGS. 9 to 11, a two-dimensional ultrasound image U currently being captured and the message M are displayed together on the monitor 23.

As described above, since the scanning guide unit 28 guides the user to perform the scanning with the ultrasound probe 1 for the target position and the target posture angle for imaging the recommended cross section R present in the three-dimensional ultrasound image T generated from the plurality of two-dimensional ultrasound images U actually captured for the subject, the user can easily visualize the recommended cross section R regardless of the skill level of the examination by moving the ultrasound probe 1 in accordance with the guide of the scanning guide unit 28 and adjusting the posture angle thereof even in a case in which there is individual differences in the shape, the size, and the disposition position of the organ as the examination target for each subject.

Under the control of the body controller 29, the display controller 22 performs predetermined processing on the two-dimensional ultrasound image U sent from the two-dimensional ultrasound image generation unit 21, information for guiding the ultrasound probe 1, which is output from the scanning guide unit 28, and the like, and displays the processed information on the monitor 23.

The monitor 23 displays the ultrasound image and the information for guiding the scanning with the ultrasound probe 1 under the control of the display controller 22, and includes, for example, a display device such as a liquid crystal display (LCD) or an organic electroluminescence display (organic EL display).

The body controller 29 controls each unit of the apparatus body 2, the transceiver circuit 12 of the ultrasound probe 1, and the position/posture sensor 13 based on a control program and the like stored in advance.

The input device 30 is an input device for the user to perform an input operation, and is configured by, for example, a device such as a keyboard, a mouse, a trackball, a touchpad, and a touch sensor disposed in a state of being superimposed on the monitor 23.

It should be noted that the processor 32 including the two-dimensional ultrasound image generation unit 21, the display controller 22, the sensor information analysis unit 24, the three-dimensional ultrasound image generation unit 25, the arbitrary cross section image generation unit 26, the cross section determination unit 27, the scanning guide unit 28, and the body controller 29 is configured by a central processing unit (CPU) and the control program for causing the CPU to execute various types of processing, but the processor 32 may be configured by a field programmable gate array (FPGA), a digital signal processor (DSP), an application specific integrated circuit (ASIC), a graphics processing unit (GPU), or other integrated circuits (IC), or may be configured by a combination thereof.

In addition, the two-dimensional ultrasound image generation unit 21, the display controller 22, the sensor information analysis unit 24, the three-dimensional ultrasound image generation unit 25, the arbitrary cross section image generation unit 26, the cross section determination unit 27, the scanning guide unit 28, and the body controller 29 can also be configured by being partially or entirely integrated into one CPU or the like.

Next, an operation of the ultrasound diagnostic apparatus according to Embodiment 1 will be described with reference to the flowchart shown in FIG. 12. Hereinafter, a case will be described in which a specific organ is selected as the examination target of the subject, and the recommended cross section R corresponding to the selected organ is stored by the cross section determination unit 27. It should be noted that organ as the examination target can be selected by the user via the input device 30 before the examination starts. It is assumed that the user continuously changes the position and the posture angle of the ultrasound probe 1 in order to visualize the organ as the examination target.

In step S1, the position and the posture angle of the ultrasound probe 1 are detected. In this case, the position/posture sensor 13 acquires a signal representing the current position and the current posture angle of the ultrasound probe 1, and the sensor information analysis unit 24 acquires information representing the position and the posture angle of the ultrasound probe 1 by analyzing the signal acquired by the position/posture sensor 13. The information representing the position and the posture angle of the ultrasound probe 1 acquired in this way is sent to the three-dimensional ultrasound image generation unit 25.

In step S2, the two-dimensional ultrasound image generation unit 21 generates the two-dimensional ultrasound image U at the current position and the current posture angle of the ultrasound probe 1. In this case, under the control of the body controller 29, the transmission and reception of the ultrasound from the plurality of transducers of the transducer array 11 are started in accordance with the drive signal from the pulser 41 of the transceiver circuit 12 of the ultrasound probe 1, the ultrasound echo from the subject is received by the plurality of transducers of the transducer array 11, and the reception signal as the analog signal is output to the amplifying unit 42, is amplified, and then is subjected to the AD conversion via the AD conversion unit 43 to acquire the reception data.

The reception focus processing is performed on the reception data by the beam former 44, and the sound ray signal generated by the reception focusing processing is sent to the two-dimensional ultrasound image generation unit 21 of the apparatus body 2, thereby the two-dimensional ultrasound image U representing the tomographic image information of the subject is generated by the two-dimensional ultrasound image generation unit 21. In this case, the signal processing unit 45 of the two-dimensional ultrasound image generation unit 21 performs the correction of the attenuation in accordance with the depth of the reflection position of the ultrasound and the envelope detection processing on the sound ray signal, the DSC 46 performs the conversion into the image signal in accordance with the normal television signal scanning method, and the image processing unit 47 performs various types of necessary image processing such as gradation processing. The two-dimensional ultrasound image generated in step S2 in this way is displayed on the monitor 23 via the display controller 22 and is sent to the three-dimensional ultrasound image generation unit 25.

In step S3, the three-dimensional ultrasound image generation unit 25 determines whether or not the two-dimensional ultrasound image U for generating the three-dimensional ultrasound image T is sufficiently obtained. For example, the three-dimensional ultrasound image generation unit 25 can determine that the two-dimensional ultrasound images U are sufficiently obtained in a case in which a predetermined number of two-dimensional ultrasound images U, such as 100 frames, are obtained, and can determine that the two-dimensional ultrasound images U are not sufficiently obtained in a case in which the predetermined number of two-dimensional ultrasound images U are not obtained.

In addition, the three-dimensional ultrasound image generation unit 25 can determine that the two-dimensional ultrasound image U is sufficiently obtained in a case in which a predetermined time, for example, 5 seconds or the like has elapsed from, for example, a point in time at which the examination is started, a point in time at which the ultrasound probe 1 comes into contact with the body surface of the subject from the start of the examination, or a point in time at which an instruction to start the examination is input by the user via the input device 30, and can determine that the two-dimensional ultrasound image U is not sufficiently obtained in a case in which the predetermined time has not elapsed. It should be noted that, for example, in a case in which the two-dimensional ultrasound image U in which the structure inside the subject is shown is obtained from a state in which the two-dimensional ultrasound image U in which the entire ultrasound probe 1 is filled with black or the like is obtained by the ultrasound probe 1 leaving the body surface of the subject, the three-dimensional ultrasound image generation unit 25 can determine that the ultrasound probe 1 is in contact with the body surface of the subject.

In a case in which it is determined in step S3 that the two-dimensional ultrasound image U is not sufficiently obtained, the processing returns to step S1, and the position and the posture angle of the ultrasound probe 1 are newly detected. Subsequently, the two-dimensional ultrasound image U is generated in step S2, and it is determined in step S3 whether or not the two-dimensional ultrasound image U is sufficiently obtained. In this manner, the processing of step S1 to step S3 is repeated as long as it is determined in step S3 that the two-dimensional ultrasound image U is not sufficiently obtained.

In a case in which it is determined in step S3 that the two-dimensional ultrasound image U is sufficiently obtained, the processing proceeds to step S4. In step S4, the three-dimensional ultrasound image generation unit 25 generates the three-dimensional ultrasound image T based on the information indicating the position and the posture angle of the ultrasound probe 1 obtained by repeatedly performing steps S1 to S3 and the plurality of two-dimensional ultrasound images U. In this case, the three-dimensional ultrasound image generation unit 25 can generate the three-dimensional ultrasound image T by arranging the plurality of two-dimensional ultrasound images U in the three-dimensional space in accordance with, for example, information indicating the position and the posture angle of the ultrasound probe 1.

In step S5, the arbitrary cross section image generation unit 26 determines whether or not the three-dimensional ultrasound image T having a sufficient size is obtained such that a sufficient number of arbitrary cross section images A can be cut out in the steps to be performed later. The arbitrary cross section image generation unit 26 can determine that the three-dimensional ultrasound image T having a sufficient size is obtained, for example, in a case in which the volume of the three-dimensional ultrasound image T is equal to or greater than a predetermined volume, and can determine that the three-dimensional ultrasound image T having a sufficient size is not obtained in a case in which the volume of the three-dimensional ultrasound image T is less than the predetermined volume. A threshold value of the volume of the three-dimensional ultrasound image T can be set for each organ, and, for example, in a case in which the organ as the examination target is the liver, the threshold value of the volume of the three-dimensional ultrasound image T can be set to 5 cm×5 cm×5 cm=125 $cm^3$ or the like. Further, the threshold value of the volume of the three-dimensional ultrasound image T can also be set by the number of voxels.

In a case in which it is determined in step S5 that the three-dimensional ultrasound image T having a sufficient size is not obtained, the processing returns to step S1, and then the processing of step S2 to step S4 is newly performed, so that the three-dimensional ultrasound image T generated in step S4 of the next time is added to the three-dimensional ultrasound image T generated in step S4 of the previous time. Therefore, the three-dimensional ultrasound image T after step S4 of the second time is larger than the three-dimensional ultrasound image T generated in step S4 of the first time. In a case in which the processing of step S4 is completed for the second time, the processing proceeds to step S5, and it is determined whether or not the three-dimensional ultrasound image T having a sufficient size is obtained.

In this manner, as long as it is determined in step S5 that the three-dimensional ultrasound image T having a sufficient size is not obtained, the processing of step S1 to step S5 is repeated, and the three-dimensional ultrasound image T obtained as a result is gradually increased.

In a case in which it is determined in step S5 that the three-dimensional ultrasound image T having a sufficient size is obtained, the processing proceeds to step S6. In step S6, the arbitrary cross section image generation unit 26 cuts out the plurality of arbitrary cross section images A from the three-dimensional ultrasound image T obtained in steps S1 to S5, to generate the plurality of arbitrary cross section images A. In this case, the arbitrary cross section image generation unit 26 can cut out the arbitrary cross section image A at a plurality of positions and angles by, for example, combining the methods shown in FIGS. 4 to 7.

In step S7, the cross section determination unit 27 determines whether or not any one of the plurality of arbitrary cross section images A generated in step S6 represents the recommended cross section R. The cross section determination unit 27 can calculate the matching degree between the image pattern of the recommended cross section R and the image patterns of the plurality of arbitrary cross section images A by using, for example, a trained model in machine learning, which has learned the relationship between the recommended cross section R and the large number of arbitrary cross section images A, and determine that any one of the plurality of arbitrary cross section images A represents the recommended cross section R in a case in which there is the arbitrary cross section image A of which the calculated matching degree exceeds the threshold value. The cross section determination unit 27 can also calculate the matching degree between the image pattern of the recommended cross section R and the image pattern of the arbitrary cross section image A by using, for example, the template matching method for the image pattern of the recommended cross section R and the image pattern of the arbitrary cross section image A stored in advance, instead of using the trained model.

In general, the shape, the size, the disposition position, and the like of the organ are different for each subject, but the three-dimensional ultrasound image T generated in step S4 is generated based on the plurality of two-dimensional ultrasound images U obtained by actually imaging the inside of the subject, so that it is possible to obtain the position and the posture angle of the ultrasound probe 1 for imaging the recommended cross section R unique to the subject in a case in which the arbitrary cross section image A representing the recommended cross section R is present in the three-dimensional ultrasound image T.

In a case in which it is determined in step S7 that none of the plurality of arbitrary cross section images A represents the recommended cross section R, the processing returns to step S1. In step S4, a larger three-dimensional ultrasound image T is obtained, and in step S6 following step S5, the plurality of arbitrary cross section images A are newly cut out from the three-dimensional ultrasound image T and generated. In a case in which step S6 is completed, the processing of step S7 is performed. In this manner, the processing of step S1 to step S7 is repeated as long as it is determined in step S7 that none of the plurality of arbitrary cross section images A represents the recommended cross section R.

In a case in which it is determined in step S7 that any one of the plurality of arbitrary cross section images A represents the recommended cross section R, the processing proceeds to step S8. In step S8, the scanning guide unit 28 uses the position and the posture angle of the ultrasound probe 1 for capturing the arbitrary cross section image A determined to represent the recommended cross section R in step S7 as the target position and the target posture angle of the ultrasound probe 1 for capturing the two-dimensional ultrasound image U representing the recommended cross section R, and guides the user to perform the scanning with the ultrasound probe 1 toward the target position and the target posture angle.

In this case, the scanning guide unit 28 can display a message M for guiding the scanning with the ultrasound probe 1 on the monitor 23, for example, as shown in FIGS. 9 to 11. The user can easily visualize the recommended cross section R regardless of the skill level of the examination by moving the ultrasound probe 1 and adjusting the posture angle of the ultrasound probe 1 under the guide of the scanning guide unit 28.

In following step S9, the body controller 29 determines whether or not to end the examination of the subject. The body controller 29 can determine to end the examination in a case in which the user inputs an instruction to end the examination via the input device 30, for example, because the recommended cross section R can be visualized, and determine to continue the examination in a case in which the instruction to end the examination is not particularly input. In a case in which it is determined to continue the examination in step S9, the processing returns to step S1, and then the following processing of step S2 to step S9 is performed again. In a case in which it is determined to end the examination in step S9, the operation of the ultrasound diagnostic apparatus according to the flowchart of FIG. 12 is completed.

As described above, with the ultrasound diagnostic apparatus according to Embodiment 1, the three-dimensional ultrasound image generation unit 25 generates the three-dimensional ultrasound image T based on the plurality of two-dimensional ultrasound images U of the inside of the subject and the position and the posture angle of the ultrasound probe 1 in a case in which the two-dimensional ultrasound images U are captured, the arbitrary cross section image generation unit 26 cuts out the arbitrary cross section image A from the three-dimensional ultrasound image T, to generate the arbitrary cross section image A, the cross section determination unit 27 determines whether or not the arbitrary cross section image A represents the recommended cross section R, and in a case in which it is determined that the arbitrary cross section image A represents the recommended cross section R, the scanning guide unit 28 guides the user to perform the scanning with the ultrasound probe 1 toward the target position and the target posture angle of the ultrasound probe 1 for capturing the two-dimensional ultrasound image U representing the recommended cross section R, so that the recommended cross section R can be easily visualized regardless of the skill level of the user even in a case in which there are individual differences in the subject, such as the shape, the size, the disposition position, and the like of the organ as the examination target.

It should be noted that the description is made in which the ultrasound probe 1 comprises the transceiver circuit 12, but the apparatus body 2 may comprise the transceiver circuit 12.

In addition, although the description is made in which the apparatus body 2 comprises the two-dimensional ultrasound image generation unit 21, the ultrasound probe 1 may comprise the two-dimensional ultrasound image generation unit 21.

In addition, the apparatus body 2 may be a so-called stationary type, a portable type that is easily carried, or a so-called hand-held type configured by, for example, a smartphone or tablet computer. As described above, the type of the device constituting the apparatus body 2 is not particularly limited.

The description is made in which the three-dimensional ultrasound image generation unit 25 generates the three-dimensional ultrasound image T in a case in which it is determined that the two-dimensional ultrasound image U for generating the three-dimensional ultrasound image T is sufficiently obtained, but the three-dimensional ultrasound image generation unit 25 can also perform processing of sequentially generating the three-dimensional ultrasound image T by using the obtained two-dimensional ultrasound image U in an accumulative manner each time the two-dimensional ultrasound image U is generated by the two-dimensional ultrasound image generation unit 21.

In addition, the description is made in which the three-dimensional ultrasound image generation unit 25 acquires the three-dimensional ultrasound image T based on the information representing the position and the posture angle of the ultrasound probe 1 acquired by the sensor information analysis unit 24 and the plurality of two-dimensional ultrasound images U, but the three-dimensional ultrasound image generation unit 25 can also acquire the three-dimensional ultrasound image T, for example, based on the information representing the position and the posture angle of the ultrasound probe 1 acquired by the sensor information analysis unit 24 and the signal obtained by the transceiver circuit 12.

Although not shown, the ultrasound diagnostic apparatus can comprise an image memory for storing the arbitrary cross section image A determined to represent the recommended cross section R by the cross section determination unit 27. In this case, the body controller 29 can automatically store, for example, the arbitrary cross section image A determined to represent the recommended cross section R in the image memory. In addition, the body controller 29 displays a message or the like for checking whether or not to store the arbitrary cross section image A determined to represent the recommended cross section R on the monitor 23, and the arbitrary cross section image A can be stored in the image memory in a case in which the user inputs an instruction to store the arbitrary cross section image A via the input device 30.

As information for guiding the scanning with the ultrasound probe 1, the scanning guide unit 28 can also display, on the monitor 23, a so-called schema image in which the target position and the target posture angle of the ultrasound probe 1 for capturing the two-dimensional ultrasound image U representing the recommended cross section and the current position and the current posture angle of the ultrasound probe 1 are superimposed. The schema image is an image imitating a part of a human body. The user can easily understand a relationship between the current position and the current posture angle of the ultrasound probe 1 and the target position and the target posture angle by checking the schema image.

In addition, although the description is made in which the scanning guide unit 28 guides the user to perform the scanning with the ultrasound probe 1 by displaying the message M on the monitor 23, the method of guiding the scanning with the ultrasound probe 1 is not particularly limited to this. For example, in a case in which the ultrasound diagnostic apparatus comprises a speaker (not shown), the scanning guide unit 28 can also guide the scanning with the ultrasound probe 1 by voice via the speaker.

In addition, the matching degree between each of the plurality of arbitrary cross section images A and one recommended cross section image R may exceed a threshold value. In this case, the cross section determination unit 27 can determine, for example, the arbitrary cross section image A of which the matching degree is the highest as the arbitrary cross section image A representing the recommended cross section R. In addition, the cross section determination unit 27 can also present a list of the arbitrary cross section images A of which the matching degree exceeds the threshold value to the user by displaying the list on the monitor 23, and then allow the user to select one arbitrary cross section image A via the input device 30. The arbitrary cross section image A selected by the user in this way is determined as the arbitrary cross section image A representing the recommended cross section R.

In addition, the cross section determination unit 27 can store a plurality of different recommended cross sections R in advance. Here, storing the plurality of different recommended cross sections R in advance represents any one of learning the image patterns of the plurality of different recommended cross sections R in advance via a trained model in machine learning or storing the image patterns of the plurality of different recommended cross sections R in advance as images. The cross section determination unit 27 can calculate the matching degree between the image pattern of the arbitrary cross section image A and the image pattern of each of the plurality of recommended cross sections R, and determine the arbitrary cross section image A of which the matching degree exceeds the threshold value as the arbitrary cross section image A representing the recommended cross section R used to calculate the matching degree.

Further, in this case, in a case in which a plurality of rates of match calculated in a plurality of combinations of the image pattern of the arbitrary cross section image A and the image pattern of the recommended cross section R exceed the threshold value, that is, in a case in which it is determined that the plurality of arbitrary cross section images A represent a plurality of different recommended cross sections R. In this case, the scanning guide unit 28 can guide the scanning toward the target position and the target posture angle of the ultrasound probe 1 for capturing the two-dimensional ultrasound image U representing the recommended cross section R of which the matching degree is the highest among the plurality of recommended cross sections R, for example. In addition, the scanning guide unit 28 can also present, for example, a list of the recommended cross sections R of which the matching degree exceeds the threshold value to the user by displaying the list on the monitor 23, and then allow the user to select one recommended cross section R via the input device 30. The scanning guide unit 28 can guide the scanning toward the target position and the target posture angle of the ultrasound probe 1 for capturing the two-dimensional ultrasound image U representing the recommended cross section R selected by the user.

In addition, in a case in which the plurality of different recommended cross sections R are stored, the cross section determination unit 27 can set the recommended cross section R that has been imaged among the plurality of different recommended cross sections R as a target not to be determined whether or not the arbitrary cross section image A represents the recommended cross section R. As a result, it is possible to prevent the user from re-examining the recommended cross section R that has already been examined, and to smoothly examine the plurality of recommended cross sections R.

In addition, the cross section determination unit 27 can also store in advance the target position and the target posture angle for imaging the plurality of different recommended cross sections R in association with the plurality of different recommended cross sections R. In this case, in a case in which the cross section determination unit 27 determines that the arbitrary cross section image A represents the recommended cross section R that has been imaged among the plurality of different recommended cross sections R, the scanning guide unit 28 can guide the user to perform the scanning with the ultrasound probe 1 toward the target position and the target posture angle corresponding to the recommended cross section R that has not yet been imaged.

In this case, the scanning guide unit 28 can guide the scanning with the ultrasound probe 1 toward the target position and the target posture angle corresponding to the recommended cross section R closest to the current position of the ultrasound probe 1 among the plurality of recommended cross sections R that have not yet been imaged. In addition, the scanning guide unit 28 can display a list of the plurality of recommended cross sections R that have not yet been imaged on the monitor 23, allow the user to select one recommended cross section R via the input device 30, and then guide the scanning with the ultrasound probe 1 toward the target position and the target posture angle corresponding to the recommended cross section R selected by the user.

In addition, the priority of the examination can be determined in advance for the plurality of different recommended cross sections R. This priority can be determined, for example, by the user inputting the priority in advance via the input device 30. In a case in which the cross section determination unit 27 determines that the arbitrary cross section image A represents the recommended cross section R that has been imaged among the plurality of different recommended cross sections R, the scanning guide unit 28 can guide the scanning with the ultrasound probe 1 toward the target position and the target posture angle corresponding to the recommended cross section R that has not yet been imaged, in accordance with the priority.

The cross section determination unit 27 can also store in advance the plurality of different recommended cross sections R, an indicator cross section different from the plurality of different recommended cross sections R, and a correspondence relationship between the target position and the target posture angle of the ultrasound probe 1 for imaging the plurality of different recommended cross sections R and the position and the posture angle of the ultrasound probe 1 for imaging the indicator cross section. The indicator cross section is a cross section including the image pattern representing a characteristic structure different from the plurality of recommended cross sections R.

In this case, the cross section determination unit 27 can calculate the matching degree between the image patterns of the plurality of different recommended cross sections R and the image pattern of the arbitrary cross section image A, and the matching degree between the image pattern of the indicator cross section and the image pattern of the arbitrary cross section image A. The scanning guide unit 28 can guide, in a case in which the matching degree between the image pattern of the indicator cross section and the image pattern of the arbitrary cross section image A exceeds a predetermined threshold value, the user to perform the scanning toward the position and the posture angle of the ultrasound probe 1 for capturing the two-dimensional ultrasound image U representing the indicator cross section, and then guide the scanning with the ultrasound probe 1 toward the target position and the target posture angle corresponding to any one of the plurality of recommended cross sections R based on the correspondence relationship between the position and the posture angle and the target position and the target posture angle corresponding to the plurality of recommended cross sections R.

Further, in this case, the scanning guide unit 28 can guide the scanning toward the target position and the target posture angle of the ultrasound probe 1 corresponding to the recommended cross section R closest to the position of the ultrasound probe 1 for imaging the indicator cross section, for example. In addition, the scanning guide unit 28 can also guide the scanning toward the target position and the target posture angle of the ultrasound probe 1 corresponding to the recommended cross section R closest to the position of the ultrasound probe 1 for imaging the indicator cross section among the plurality of recommended cross sections R that have not yet been imaged, for example. In addition, the scanning guide unit 28 can display a list of the plurality of recommended cross sections R that have not yet been imaged on the monitor 23, allow the user to select one of the recommended cross sections R via the input device 30, and then guide the scanning with the ultrasound probe 1 toward the target position and the target posture angle corresponding to the recommended cross section R selected by the user. In addition, in a case in which the priority of the examination is determined in advance for the plurality of recommended cross sections R, the scanning guide unit 28 can also guide the scanning with the ultrasound probe 1 toward the target position and the target posture angle corresponding to the recommended cross section R in accordance with the priority.

In addition, the description is made in which the user designates the organ as the examination target in advance before the examination is started, but, for example, a part of the organ and a scanning location or a scanning method thereof, such as a so-called right subcostal scanning of the prehepatic upper segment, can also be designated in addition to the name of the organ to be designated as the examination target is not limited.

Instead of manually designating the examination target by the user, the examination target can be specified by analyzing the captured two-dimensional ultrasound image U via the ultrasound diagnostic apparatus. For example, the apparatus body 2 can comprise an examination target specifying unit (not shown) that specifies the examination target from the two-dimensional ultrasound image U. The examination target specifying unit is connected to, for example, the two-dimensional ultrasound image generation unit 21, the cross section determination unit 27, and the body controller 29. The examination target specifying unit can detect a structure in the two-dimensional ultrasound image U by using, for example, a trained model in machine learning, which has learned a large number of two-dimensional ultrasound images U of a plurality of examination targets, and an image analysis technique using a feature amount such as template matching, AdaBoost, a support-vector machine (SVM), or a scale invariant feature transform (SIFT), and can specify the type of the structure. In this case, for example, the body controller 29 can specify the examination target based on the type of the structure specified by the examination target specifying unit.

Embodiment 2

In Embodiment 1, the position/posture detection unit that detects the position and the posture angle of the ultrasound probe 1 is configured by the position/posture sensor 13 and the sensor information analysis unit 24, but, for example, the position and the posture angle of the ultrasound probe 1 can also be detected by analyzing the two-dimensional ultrasound image U.

Figure 13:
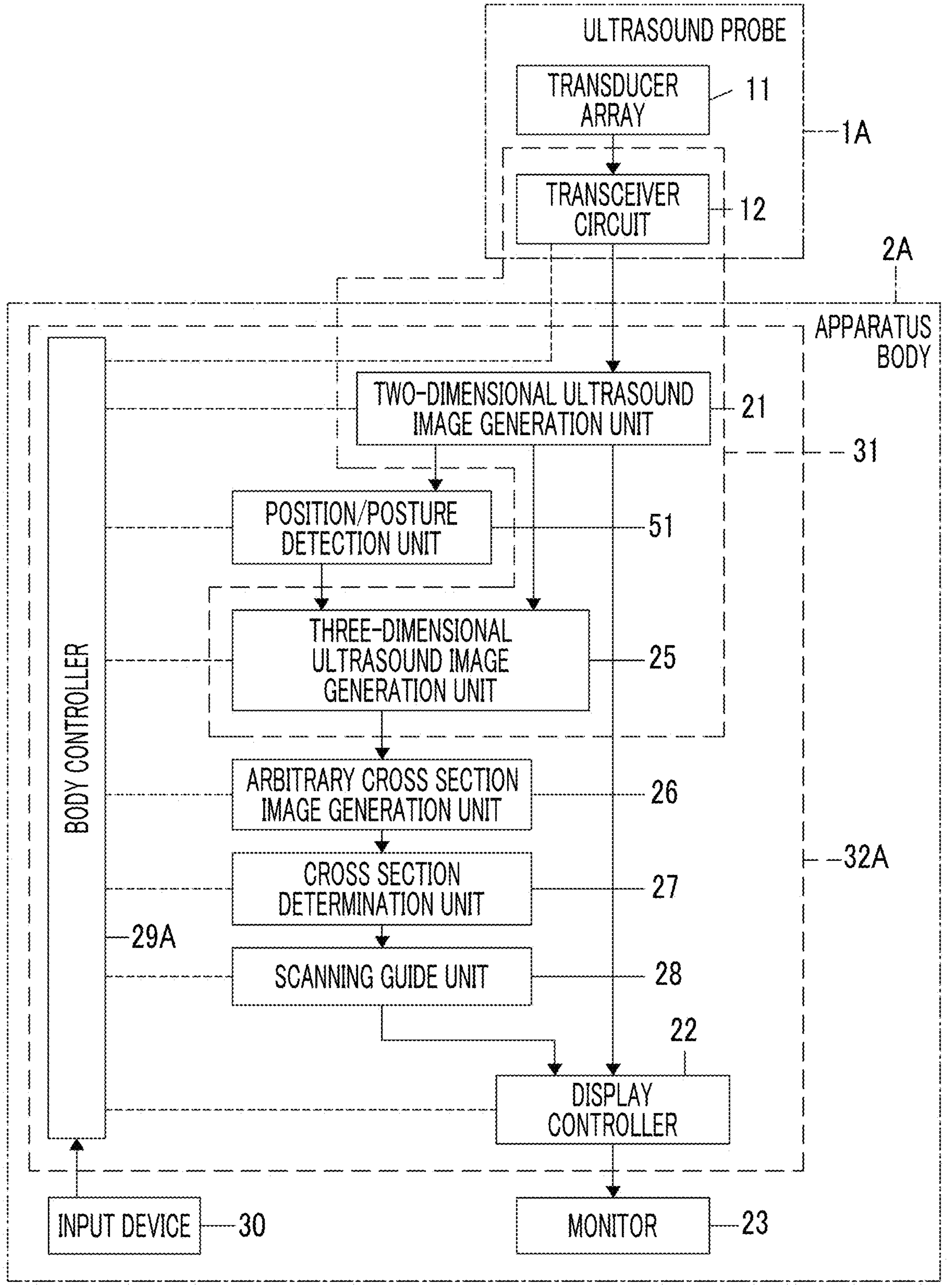
FIG. 13 is a block diagram showing a configuration of an ultrasound diagnostic apparatus according to Embodiment 2 of the present invention.

FIG. 13 shows a configuration of an ultrasound diagnostic apparatus according to Embodiment 2. The ultrasound diagnostic apparatus according to Embodiment 2 comprises an ultrasound probe 1A instead of the ultrasound probe 1 and comprises an apparatus body 2A instead of the apparatus body 2, with respect to the ultrasound diagnostic apparatus according to Embodiment 1 shown in FIG. 1.

The ultrasound probe 1A according to Embodiment 2 is obtained by excluding the position/posture sensor 13 from the ultrasound probe 1 according to Embodiment 1.

The apparatus body 2A according to Embodiment 2 comprises a position/posture detection unit 51 instead of the sensor information analysis unit 24 and comprises a body controller 29A instead of the body controller 29, with respect to the apparatus body 2 according to Embodiment 2. In the apparatus body 2A, the position/posture detection unit 51 is connected to the two-dimensional ultrasound image generation unit 21. The position/posture detection unit 51 is connected to the three-dimensional ultrasound image generation unit 25 and the body controller 29A. In addition, the two-dimensional ultrasound image generation unit 21, the display controller 22, the three-dimensional ultrasound image generation unit 25, the arbitrary cross section image generation unit 26, the cross section determination unit 27, the scanning guide unit 28, the body controller 29A, and the position/posture detection unit 51 constitute a processor 32A for the apparatus body 2A.

The position/posture detection unit 51 detects the position and the posture angle of the ultrasound probe 1A in a case in which the two-dimensional ultrasound image U is generated, by performing image analysis on the two-dimensional ultrasound image U generated by the two-dimensional ultrasound image generation unit 21. The position/posture detection unit 51 can detect the position and the posture angle of the ultrasound probe 1A by using, for example, a trained model in machine learning, which has learned a relationship between a large number of two-dimensional ultrasound images U of the inside of the subject and the position and the posture angle of the ultrasound probe 1A in a case in which the two-dimensional ultrasound images U are captured. In addition, for example, the position/posture detection unit 51 can store the plurality of two-dimensional ultrasound images U of the inside of the subject associated with the position and the posture angle of the ultrasound probe 1A as templates, and apply a template matching method to the plurality of two-dimensional ultrasound images U stored in advance and the two-dimensional ultrasound image U newly generated by the two-dimensional ultrasound image generation unit 21, to detect the position and the posture angle of the ultrasound probe 1A.

The position and the posture angle of the ultrasound probe 1A detected by the position/posture detection unit 51 in this manner are sent to the three-dimensional ultrasound image generation unit 25, and are used for generating the three-dimensional ultrasound image T. Thereafter, the arbitrary cross section image A is cut out from the three-dimensional ultrasound image T by the arbitrary cross section image generation unit 26, and the cross section determination unit 27 determines whether or not the arbitrary cross section image A represents the recommended cross section R. Further, in a case in which the cross section determination unit 27 determines that the arbitrary cross section image A represents the recommended cross section R, the scanning guide unit 28 guides the scanning toward the target position and the target posture angle of the ultrasound probe 1A for imaging the recommended cross section R.

As described above, as in the ultrasound diagnostic apparatus according to Embodiment 2, even in a case in which the two-dimensional ultrasound image U is analyzed to detect the position and the posture angle of the ultrasound probe 1A, the scanning guide unit 28 guides the user to perform the scanning with the ultrasound probe 1 toward the target position and the target posture angle of the ultrasound probe 1 for capturing the two-dimensional ultrasound image U representing the recommended cross section R, so that the recommended cross section R can be easily visualized regardless of the skill level of the user even in a case in which there are individual differences in the subject, such as the shape, the size, the disposition position, and the like of the organ as the examination target.

Embodiment 3

Since the three-dimensional ultrasound image T is generated from the plurality of two-dimensional ultrasound images U generated in a state in which the user manually moves the ultrasound probe 1, a quality of a resolution and the like of the arbitrary cross section image A cut out from the three-dimensional ultrasound image T may be affected by how the user moves the ultrasound probe 1. For example, in a situation in which the arbitrary cross section image A is viewed for reference of the examination, it is preferable that the arbitrary cross section image A has a certain quality.

Figure 14:
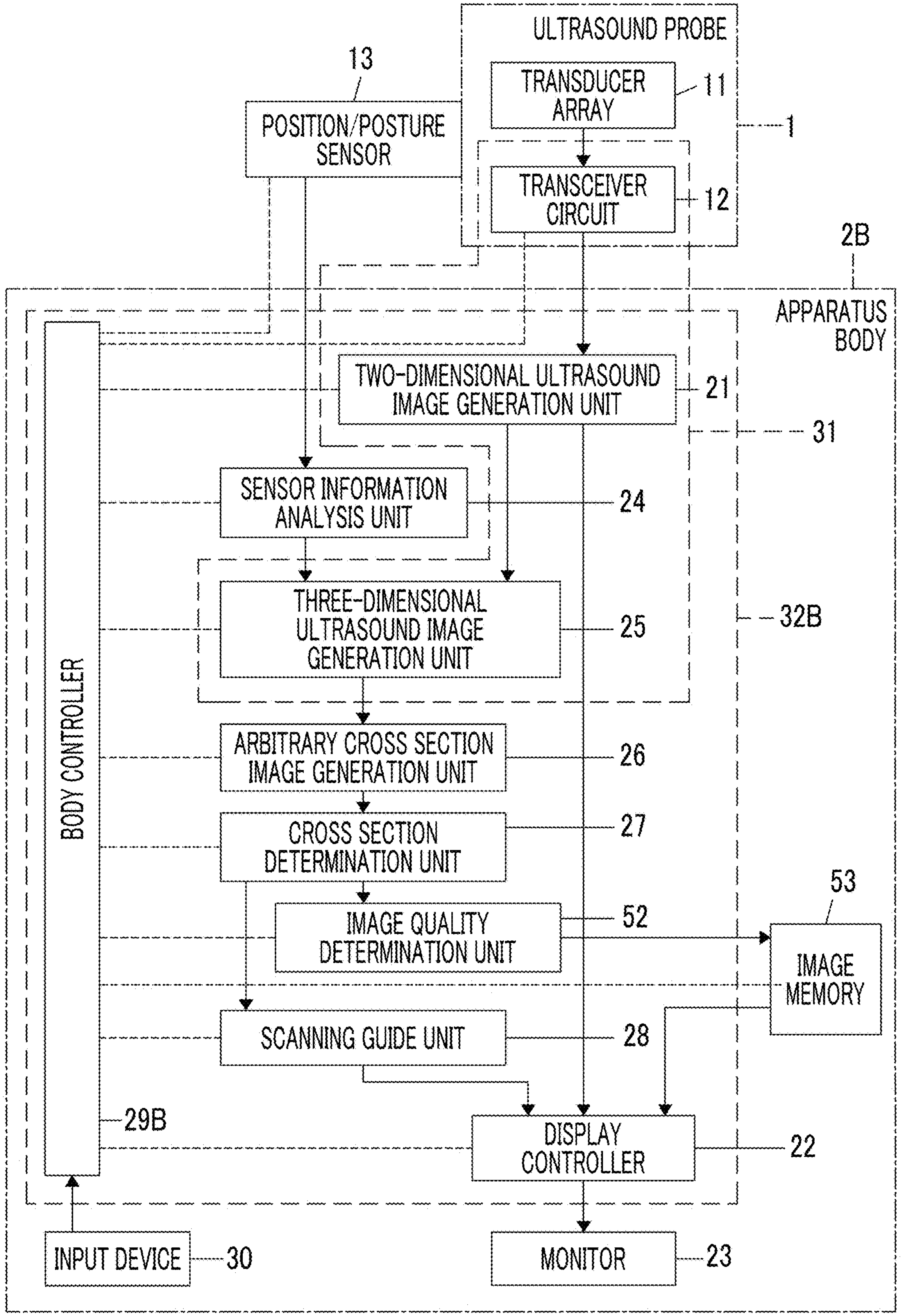
FIG. 14 is a block diagram showing a configuration of an ultrasound diagnostic apparatus according to Embodiment 3 of the present invention.

FIG. 14 shows a configuration of an ultrasound diagnostic apparatus according to Embodiment 3. The ultrasound diagnostic apparatus according to Embodiment 3 comprises an apparatus body 2B instead of the apparatus body 2 with respect to the ultrasound diagnostic apparatus according to Embodiment 1 shown in FIG. 1. The apparatus body 2B according to Embodiment 3 further comprises an image quality determination unit 52 and an image memory 53 and comprises a body controller 29B instead of the body controller 29, with respect to the apparatus body 2 according to Embodiment 1.

In the apparatus body 2B, the image quality determination unit 52 is connected to the cross section determination unit 27. The image memory 53 and the body controller 29B are connected to the image quality determination unit 52. In addition, the image memory 53 is connected to the display controller 22 and the body controller 29B. In addition, the two-dimensional ultrasound image generation unit 21, the display controller 22, the sensor information analysis unit 24, the three-dimensional ultrasound image generation unit 25, the arbitrary cross section image generation unit 26, the cross section determination unit 27, the scanning guide unit 28, the body controller 29B, and the image quality determination unit 52 constitute a processor 32B for the apparatus body 2B.

The image quality determination unit 52 determines whether or not the quality of the arbitrary cross section image A determined to represent the recommended cross section R by the cross section determination unit 27 is superior. The image quality determination unit 52 can determine whether the quality of the arbitrary cross section image A is superior, for example, by determining whether the resolution of the arbitrary cross section image A is sufficiently high or whether or not there is a defect or misregistration in a part of the image pattern of the arbitrary cross section image A.

For example, in a case in which the user moves the ultrasound probe 1 along the body surface of the subject, an interval between the two-dimensional ultrasound images U continuously generated by a frame rate in a case in which the two-dimensional ultrasound image U is generated is changed in accordance with the speed at which the ultrasound probe 1 is moved. The resolution of the arbitrary cross section image A cut out from the three-dimensional ultrasound image T is higher as the interval is smaller, and the resolution of the arbitrary cross section image A is lower as the interval is larger. Therefore, for example, the image quality determination unit 52 can calculate the reciprocal of the interval between the continuously generated two-dimensional ultrasound images U as the resolution of the arbitrary cross section image A, determine that the quality of the arbitrary cross section image A is superior in a case in which the calculated resolution is equal to or greater than a predetermined threshold value, and determine that the quality of the arbitrary cross section image A is not superior in a case in which the calculated resolution is less than the predetermined threshold value.

In addition, in a case in which the three-dimensional ultrasound image generation unit 25 performs processing of interpolating between the plurality of two-dimensional ultrasound images U arranged in the three-dimensional space in generating the three-dimensional ultrasound image T, the image quality determination unit 52 can determine that the quality of the arbitrary cross section image A is not superior, for example, in a case in which the volume of the interpolated region is equal to or greater than a predetermined threshold value, and determine that the quality of the arbitrary cross section image A is superior in a case in which the volume of the interpolated region is less than the predetermined threshold value.

In addition, for example, the image quality determination unit 52 can determine whether or not there is a defect or misregistration in a part of the image pattern of the arbitrary cross section image A by performing image analysis such as continuity of edges of a structure in the image pattern of the arbitrary cross section image A using an algorithm such as a known binarization method and contour tracking method, an algorithm using a so-called feature amount, or a trained model in machine learning. In this case, the image quality determination unit 52 can determine that the quality of the arbitrary cross section image A is not superior in a case in which it is determined that there is the defect or the misregistration in a part of the arbitrary cross section image A, and determine that the quality of the arbitrary cross section image A is superior in a case in which it is determined that the defect or misregistration is not recognized in the arbitrary cross section image A.

The image memory 53 is a memory that stores the arbitrary cross section image A determined to have superior quality by the image quality determination unit 52 under the control of the body controller 29B. Here, as the image memory 53, for example, a recording medium such as a flash memory, a hard disk drive (HDD), a solid-state drive (SSD), a flexible disk (FD), a magneto-optical disk (MO disk), a magnetic tape (MT), a random-access memory (RAM), a compact disc (CD), a digital versatile disc (DVD), a secure digital card (SD card), or a universal serial bus memory (USB memory) can be used.

The arbitrary cross section image A stored in the image memory 53 can be used, for example, to be displayed on the monitor 23 for the user to view as a reference for the examination after the examination of the subject ends, or used to be pasted on a report in a case in which the user creates a report of the examination. In such an application, it is preferable that the arbitrary cross section image A has a certain level of quality or higher.

As described above, with the ultrasound diagnostic apparatus according to Embodiment 3, the image quality determination unit 52 determines the quality of the arbitrary cross section image A determined to represent the recommended cross section R, and the arbitrary cross section image A for which the image quality determination unit 52 determines that the quality is superior is stored in the image memory 53, so that, for example, after the examination of the subject, the user can refer to the high-quality arbitrary cross section image A to help the diagnosis of the subject.

It should be noted that ultrasound diagnostic apparatus according to Embodiment 3 has a configuration in which the image quality determination unit 52 and the image memory 53 are added to the apparatus body 2 in the ultrasound diagnostic apparatus according to Embodiment 1, but a configuration can also be adopted in which the image quality determination unit 52 and the image memory 53 are added to the apparatus body 2A in the ultrasound diagnostic apparatus according to Embodiment 2.

Embodiment 4

In a case in which the user who has a low skill level of the examination using the ultrasound diagnostic apparatus performs the examination of the subject, it may be difficult to scan a region in the subject including the recommended cross section R. In such a case, the ultrasound diagnostic apparatus according to the embodiment of the present invention can also prompt the user to perform the scanning with the ultrasound probe 1 such that the user can perform appropriate scanning.

Figure 15:
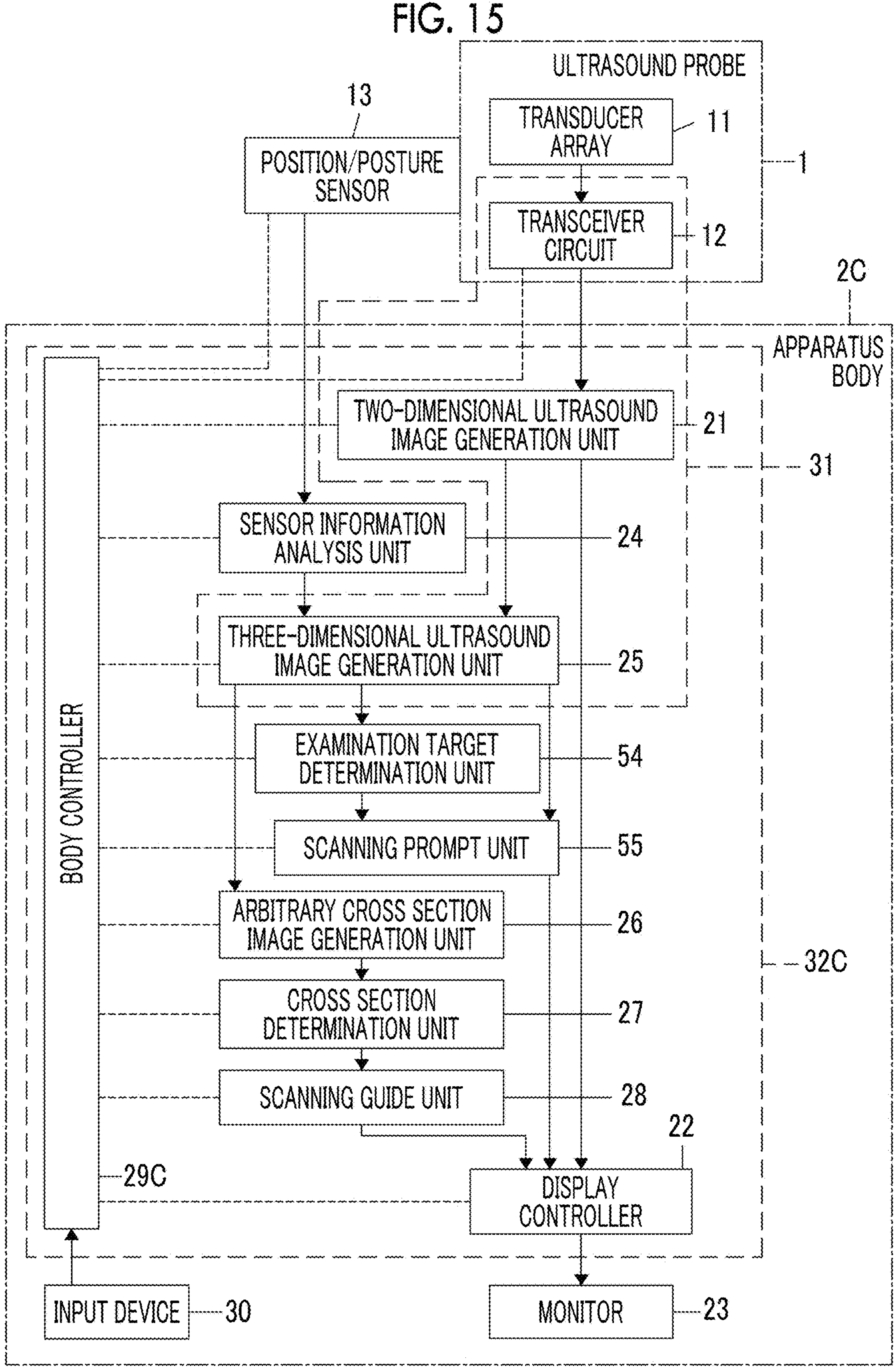
FIG. 15 is a block diagram showing a configuration of an ultrasound diagnostic apparatus according to Embodiment 4 of the present invention.

FIG. 15 shows a configuration of an ultrasound diagnostic apparatus according to Embodiment 4. The ultrasound diagnostic apparatus according to Embodiment 4 comprises an apparatus body 2C instead of the apparatus body 2 with respect to the ultrasound diagnostic apparatus according to Embodiment 1 shown in FIG. 1. The apparatus body 2C further comprises an examination target determination unit 54 and a scanning prompt unit 55 and comprises a body controller 29C instead of the body controller 29, with respect to the apparatus body 2 according to Embodiment 1.

In the apparatus body 2C, the examination target determination unit 54 and the scanning prompt unit 55 are connected to the three-dimensional ultrasound image generation unit 25. The examination target determination unit 54 is connected to the scanning prompt unit 55 and the body controller 29C. The scanning prompt unit 55 is connected to the display controller 22 and the body controller 29C. In addition, the two-dimensional ultrasound image generation unit 21, the display controller 22, the sensor information analysis unit 24, the three-dimensional ultrasound image generation unit 25, the arbitrary cross section image generation unit 26, the cross section determination unit 27, the scanning guide unit 28, the body controller 29C, the examination target determination unit 54, and the scanning prompt unit 55 constitute a processor 32C for the apparatus body 2C.

The body controller 29C registers the examination target input by the user via the input device 30. The cross section determination unit 27 determines whether or not the recommended cross section R corresponding to the examination target registered in this manner is represented by the arbitrary cross section image A.

The examination target determination unit 54 determines whether or not the ultrasound probe 1 is scanning the examination target registered by the body controller 29C by performing the image analysis on the three-dimensional ultrasound image T generated by the three-dimensional ultrasound image generation unit 25. The examination target determination unit 54 can detect a structure in the three-dimensional ultrasound image T by using, for example, a trained model in machine learning, which has learned a large number of two-dimensional ultrasound images U of the plurality of examination targets, and estimate the type of the structure using an image analysis technique using feature amounts such as template matching, AdaBoost, SVM, or SIFT.

Further, the examination target determination unit 54 can determine that the ultrasound probe 1 is scanning the examination target registered by the body controller 29C in a case in which the estimated type of the structure is recognized as the examination target registered by the body controller 29C, and determine that the ultrasound probe 1 is not scanning the examination target registered by the body controller 29C in a case in which the estimated type of the structure is not recognized as the examination target registered by the body controller 29C.

The scanning prompt unit 55 prompts the user to perform the scanning with the ultrasound probe 1 in a case in which the cross section determination unit 27 does not determine that the arbitrary cross section image A represents the recommended cross section R even after a predetermined time has elapsed since the start of the scanning with the ultrasound probe 1. For example, in a case in which a predetermined time has elapsed from a point in time at which the examination is started, a point in time at which the ultrasound probe 1 comes into contact with the body surface of the subject from the point in time at which the examination is started, or a point in time at which the user inputs an instruction to start the examination via the input device 30, the scanning prompt unit 55 can determine that the predetermined time has elapsed since the start of the scanning with the ultrasound probe 1. It should be noted that, in a case in which the two-dimensional ultrasound image U in which the structure inside the subject is shown is obtained from, for example, a state in which the two-dimensional ultrasound image U in which the entire ultrasound probe 1 is filled with black or the like is obtained by separating the ultrasound probe 1 from the body surface of the subject, the scanning prompt unit 55 can determine that the ultrasound probe 1 is in contact with the body surface of the subject.

Here, a case in which the cross section determination unit 27 does not determine that the arbitrary cross section image A represents the recommended cross section R even after the predetermined time has elapsed since the start of the scanning with the ultrasound probe 1 includes, for example, a case in which the three-dimensional ultrasound image T does not have a sufficient size of 5 cm×5 cm×5 cm=125 $cm^3$ or the like at a point in time at which the predetermined time has elapsed. In this case, the scanning prompt unit 55 can prompt the user to move the ultrasound probe 1 in the vicinity of the current position of the ultrasound probe 1 by displaying a message for moving the ultrasound probe 1 on the monitor 23, for example.

In addition, a case in which the cross section determination unit 27 does not determine that the arbitrary cross section image A represents the recommended cross section R even in a case in which the predetermined time has elapsed since the start of the scanning with the ultrasound probe 1 also includes, for example, a case in which the three-dimensional ultrasound image T has a sufficient size at a point in time at which the predetermined time has elapsed, but the examination target determination unit 54 determines that the ultrasound probe 1 has not scanned the examination target registered by the body controller 29C. In this case, the scanning prompt unit 55 can prompt the user to scan the examination target registered by the body controller 29C by, for example, changing the position of the ultrasound probe 1 and displaying a message for scanning the examination target on the monitor 23.

As described above, with the ultrasound diagnostic apparatus according to Embodiment 4, in a case in which the scanning prompt unit 55 does not determine that the arbitrary cross section image A represents the recommended cross section R by the cross section determination unit 27 even after the predetermined time has elapsed since the start of the scanning with the ultrasound probe 1, the scanning prompt unit 55 prompts the user to perform the scanning with the ultrasound probe 1, so that, for example, even the user who has a low skill level of the examination of the subject using the ultrasound diagnostic apparatus can more easily capture the recommended cross section R.

It should be noted that, although the description is made in which the scanning prompt unit 55 prompts the user by displaying a message on the monitor 23, for example, in a case in which the ultrasound diagnostic apparatus comprises a speaker (not shown), the scanning prompt unit 55 can prompt the user by voice via the speaker.

In addition, the ultrasound diagnostic apparatus according to Embodiment 4 has a configuration in which the examination target determination unit 54 and the scanning prompt unit 55 are added to the apparatus body 2 in the ultrasound diagnostic apparatus according to Embodiment 1, but a configuration can also be adopted in which the examination target determination unit 54 and the scanning prompt unit 55 are added to the apparatus body 2A in the ultrasound diagnostic apparatus according to Embodiment 2 and the apparatus body 2B in the ultrasound diagnostic apparatus according to Embodiment 3.

Embodiment 5

In a case in which the cross section determination unit 27 stores the plurality of recommended cross sections R, the information for specifying the type of the recommended cross section R represented by the arbitrary cross section image A among the plurality of recommended cross sections R can be presented to the user such that the user can easily understand the type of the recommended cross section R present in the range scanned by the ultrasound probe 1.

Figure 16:
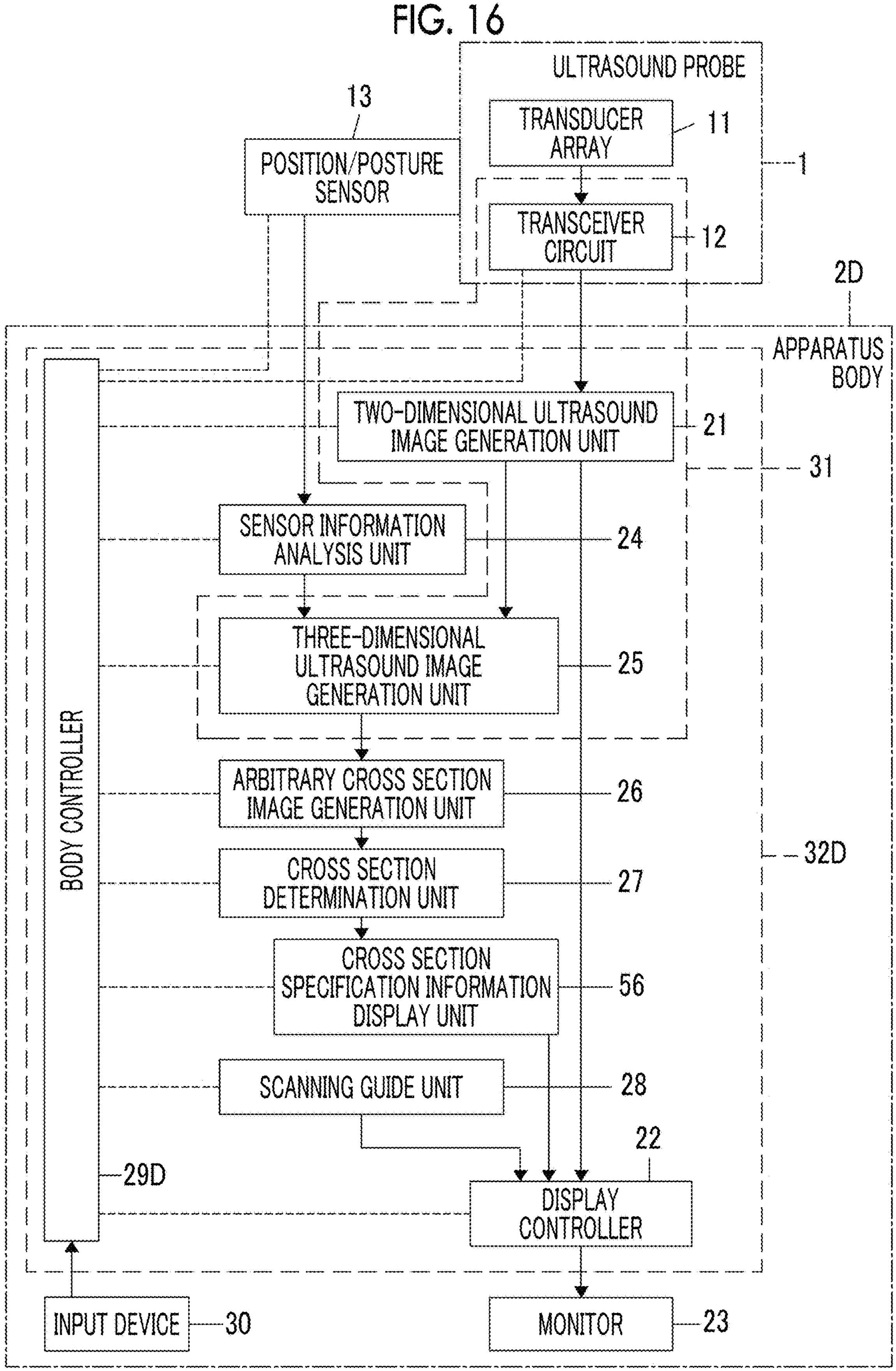
FIG. 16 is a block diagram showing a configuration of an ultrasound diagnostic apparatus according to Embodiment 5 of the present invention.

FIG. 16 shows a configuration of an ultrasound diagnostic apparatus according to Embodiment 5. The ultrasound diagnostic apparatus according to Embodiment 5 comprises an apparatus body 2D instead of the apparatus body 2 in the ultrasound diagnostic apparatus according to Embodiment 1 shown in FIG. 1. The apparatus body 2D according to Embodiment 5 further comprises a cross section specification information display unit 56 and comprises a body controller 29D instead of the body controller 29, with respect to the apparatus body 2 according to Embodiment 1.

In the apparatus body 2D, the cross section determination unit 27 is connected to the cross section specification information display unit 56. The cross section specification information display unit 56 is connected to the display controller 22 and the body controller 29D. In addition, the two-dimensional ultrasound image generation unit 21, the display controller 22, the sensor information analysis unit 24, the three-dimensional ultrasound image generation unit 25, the arbitrary cross section image generation unit 26, the cross section determination unit 27, the scanning guide unit 28, the body controller 29D, and the cross section specification information display unit 56 constitute a processor 32D for the apparatus body 2D.

The cross section determination unit 27 stores the plurality of different recommended cross sections R, and determines whether or not the arbitrary cross section image A generated by the arbitrary cross section image generation unit 26 represents any one of the plurality of recommended cross sections R.

The cross section specification information display unit 56 displays, on the monitor 23, cross section specification information for specifying the recommended cross section R determined to be represented by the arbitrary cross section image A by the cross section determination unit 27 among the plurality of different recommended cross sections R stored in the cross section determination unit 27. The cross section specification information display unit 56 can display, for example, at least one of the name of the recommended cross section R, a typical two-dimensional ultrasound image U showing the recommended cross section R, a schema image showing the recommended cross section R, or an explanatory note of the recommended cross section R on the monitor 23 as the cross section specification information.

Figure 17:
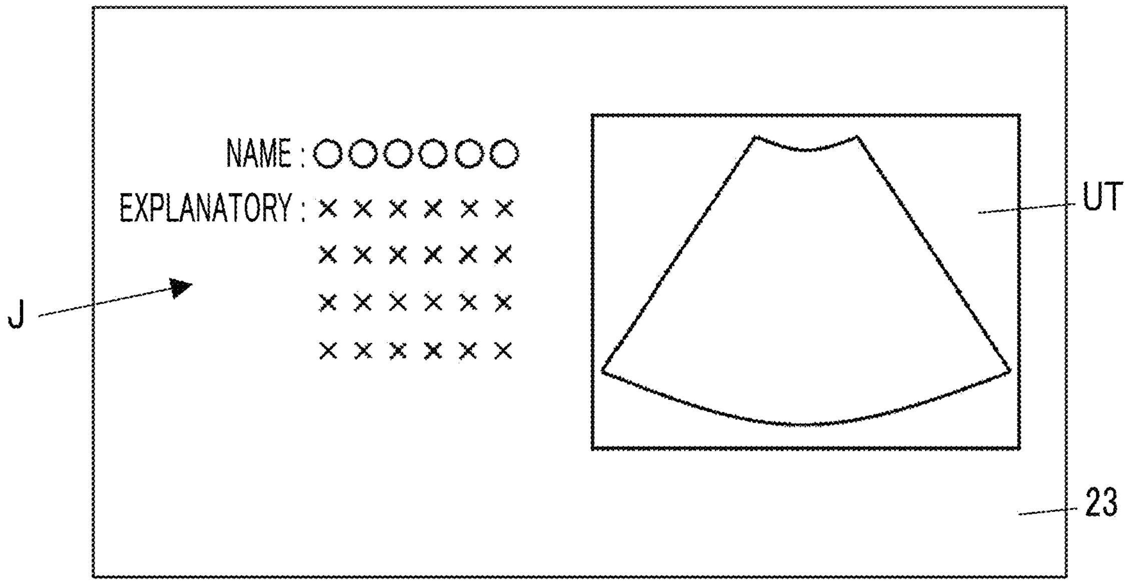
FIG. 17 is a diagram schematically showing a display example of recommended cross section specification information.

For example, as shown in FIG. 17, the cross section specification information display unit 56 can display the typical two-dimensional ultrasound image UT representing the recommended cross section R and a message J representing the name and the explanatory note of the recommended cross section R on the monitor 23 together. The cross section specification information display unit 56 can switch, for display, the cross section specification information with the two-dimensional ultrasound image U currently being captured, for example, by the input operation of the user via the input device 30, and can also display the cross section specification information and the two-dimensional ultrasound image U currently being captured together.

As described above, with the ultrasound diagnostic apparatus according to Embodiment 5, the cross section specification information display unit 56 displays the cross section specification information for specifying the recommended cross section R determined to be represented by the arbitrary cross section image A by the cross section determination unit 27 on the monitor 23, so that the user can easily understand the type of the recommended cross section R present in the range scanned by the ultrasound probe 1.

It should be noted that ultrasound diagnostic apparatus according to Embodiment 5 has a configuration in which the cross section specification information display unit 56 is added to the apparatus body 2 in the ultrasound diagnostic apparatus according to Embodiment 1, but a configuration can also be adopted in which the cross section specification information display unit 56 is added to the apparatus body 2A in the ultrasound diagnostic apparatus according to Embodiment 2, the apparatus body 2B in the ultrasound diagnostic apparatus according to Embodiment 3, and the apparatus body 2C in the ultrasound diagnostic apparatus according to Embodiment 4.

Embodiment 6

In order to more accurately image the recommended cross section R, the plurality of arbitrary cross section images A can be generated again with a narrow positional interval and a narrow angular interval in the vicinity of the arbitrary cross section image A having a certain range of the matching degree, and the determination via the cross section determination unit 27 can be further performed by using the plurality of arbitrary cross section images A that are generated again.

Figure 18:
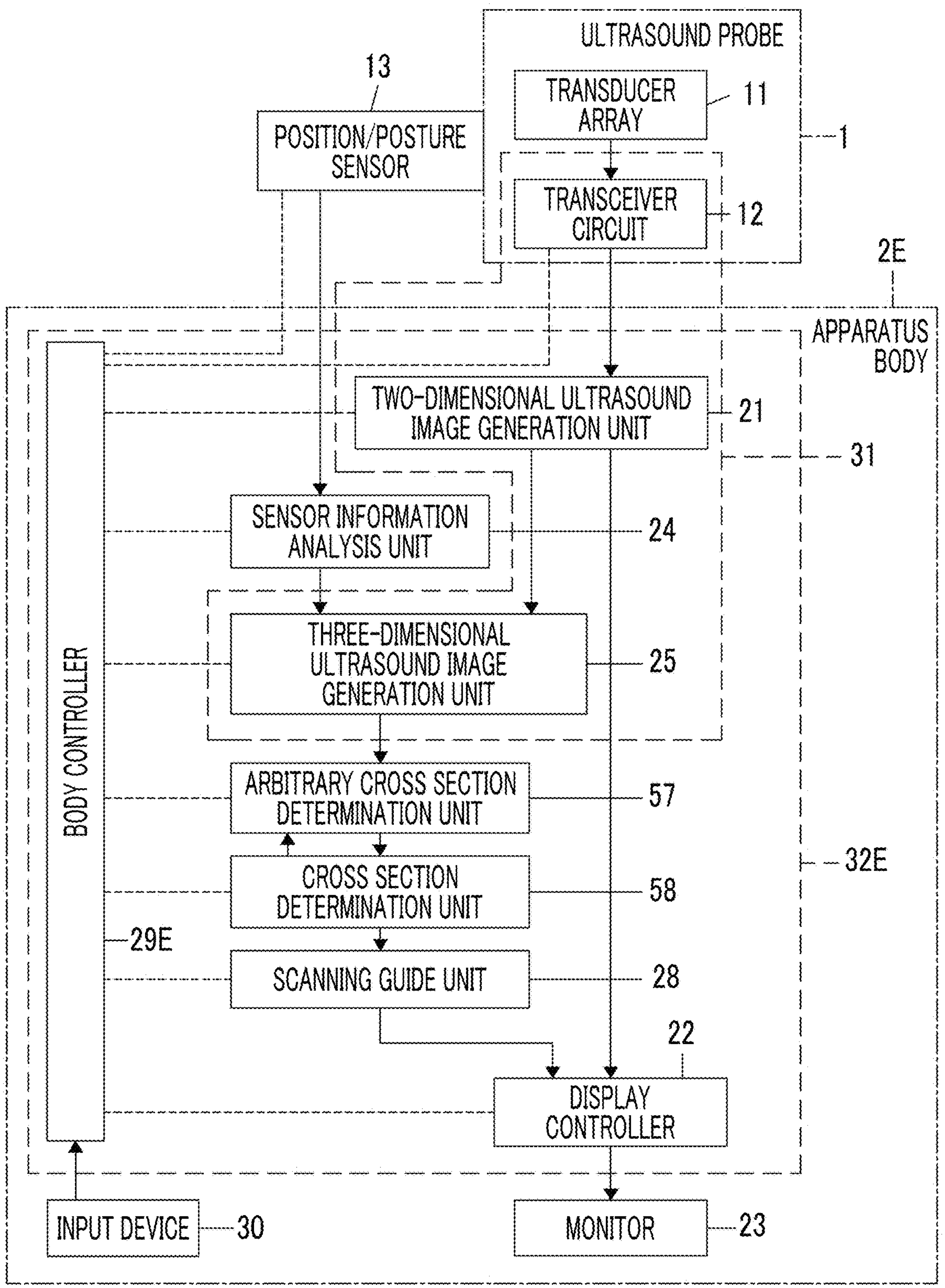
FIG. 18 is a block diagram showing a configuration of an ultrasound diagnostic apparatus according to Embodiment 6 of the present invention.

FIG. 18 shows a configuration of an ultrasound diagnostic apparatus according to Embodiment 6. The ultrasound diagnostic apparatus according to Embodiment 6 comprises an apparatus body 2E instead of the apparatus body 2 in the ultrasound diagnostic apparatus according to Embodiment 1 shown in FIG. 1. The apparatus body 2E according to Embodiment 6 comprises an arbitrary cross section image generation unit 57 instead of the arbitrary cross section image generation unit 26, comprises a cross section determination unit 58 instead of the cross section determination unit 27, and comprises a body controller 29E instead of the body controller 29, with respect to the apparatus body 2 according to Embodiment 1.

In the apparatus body 2E, the arbitrary cross section image generation unit 57 and the cross section determination unit 58 are bidirectionally connected to each other. In addition, the two-dimensional ultrasound image generation unit 21, the display controller 22, the sensor information analysis unit 24, the three-dimensional ultrasound image generation unit 25, the scanning guide unit 28, the body controller 29E, the arbitrary cross section image generation unit 57, and the cross section determination unit 58 constitute a processor 32E for the apparatus body 2E.

The arbitrary cross section image generation unit 57 can cut out two stages of the arbitrary cross section image A having different positional intervals and angular intervals from the three-dimensional ultrasound image T. The arbitrary cross section image generation unit 57 can cut out, for example, a plurality of first arbitrary cross section images at a predetermined first positional interval and a predetermined first angular interval, and cut out a plurality of second arbitrary cross section images at a second positional interval and a second angular interval narrower than the first positional interval and the first angular interval, from the three-dimensional ultrasound image T. As will be described later, the cutout of the plurality of second arbitrary cross section images is executed in a case in which the cross section determination unit 58 determines that the matching degree between the image pattern of the plurality of first arbitrary cross section images and the image pattern of the recommended cross section R is within a certain range.

For example, the arbitrary cross section image generation unit 57 can cut out, for example, about five first arbitrary cross section images every 1 cm in the X direction in a case in which the plurality of first arbitrary cross section images are cut out as in FIG. 4, can cut out, for example, about five first arbitrary cross section images every 1 cm in the Y direction in a case in which the plurality of first arbitrary cross section images are cut out as in FIG. 5, can cut out, for example, about 10 first arbitrary cross section images by rotating the first arbitrary cross section image by about 18 degrees around a rotation axis extending along the Z direction in a case in which the plurality of first arbitrary cross section images are cut out as in FIG. 6, and can cut out, for example, about 10 first arbitrary cross section images by rotating the first arbitrary cross section image by about 18 degrees around a rotation axis extending along the XY plane in a case in which the plurality of first arbitrary cross section images are cut out as in FIG. 7. The arbitrary cross section image generation unit 57 can generate a large number of first arbitrary cross section images by combining these methods.

For example, the arbitrary cross section image generation unit 57 can cut out, for example, the second arbitrary cross section images every 5 mm in the X direction in a case in which the plurality of second arbitrary cross section images are cut out as in FIG. 4, can cut out, for example, the second arbitrary cross section images every 5 mm in the Y direction in a case in which the plurality of second arbitrary cross section images are cut out as in FIG. 5, can cut out, for example, the second arbitrary cross section images by rotating the second arbitrary cross section image by about 9 degrees around a rotation axis extending along the Z direction in a case in which the plurality of second arbitrary cross section images are cut out as in FIG. 6, and can cut out, for example, the second arbitrary cross section images by rotating the second arbitrary cross section image by about 9 degrees around a rotation axis extending along the XY plane in a case in which the plurality of second arbitrary cross section images are cut out as in FIG. 7. The arbitrary cross section image generation unit 57 can generate a larger number of second arbitrary cross section images than the plurality of first arbitrary cross section images by combining these methods.

The cross section determination unit 58 has two stages of threshold values of a first threshold value and a second threshold value with respect to the matching degree between the image pattern of the arbitrary cross section image A and the image pattern of the recommended cross section R. In a case in which an upper limit of the matching degree is 100%, the first threshold value has a relatively high value, such as 70%, and the second threshold value has a value higher than the first threshold value, such as 90%. In a case in which the rates of match of all the arbitrary cross section images A are equal to or less than the first threshold value, for example, it can be determined that the recommended cross section R is not included in the region of the subject represented by the three-dimensional ultrasound image T from which the arbitrary cross section image A is cut out. In a case in which the matching degree is greater than the second threshold value, for example, it can be determined that the arbitrary cross section image A having the matching degree represents the recommended cross section R. In a case in which the matching degree is in a certain range that is greater than the first threshold value and equal to or less than the second threshold value, for example, it cannot be determined that the arbitrary cross section image A having the matching degree represents the recommended cross section R, but it can be determined that the arbitrary cross section image A representing the recommended cross section R is present at least in the vicinity of the arbitrary cross section image A.

The cross section determination unit 58 performs processing of calculating a first matching degree between the image patterns of the plurality of first arbitrary cross section images generated by the arbitrary cross section image generation unit 57 and the image pattern of the recommended cross section R, and a second matching degree between the image patterns of the plurality of second arbitrary cross section images and the image pattern of the recommended cross section R, and evaluating the calculated first matching degree and second matching degree by using the first threshold value and the second threshold value.

The cross section determination unit 58 first determines whether the first matching degree corresponding to each of the plurality of first arbitrary cross section images is equal to or less than the first threshold value, is greater than the first threshold value and equal to or less than a second threshold value, or is greater than the second threshold value.

In a case in which it is determined that all the first rates of match are equal to or less than the first threshold value, the cross section determination unit 58 determines that the recommended cross section R is not included in the region of the subject represented by the three-dimensional ultrasound image T from which the arbitrary cross section image A is cut out, and transmits an instruction to the body controller 29E to regenerate the three-dimensional ultrasound image T in order to generate the three-dimensional ultrasound image T in a region different from the region of the subject that has been scanned so far. In this case, the body controller 29E causes each unit of the ultrasound diagnostic apparatus to generate the three-dimensional ultrasound image T and to generate the plurality of first arbitrary cross section images again.

In a case in which it is determined that any one of a plurality of first rates of match is greater than the second threshold value, the cross section determination unit 58 determines that the first arbitrary cross section image having the first matching degree determined to be greater than the second threshold value represents the recommended cross section R, and transmits an instruction to the scanning guide unit 28 to guide the user to perform the scanning with the ultrasound probe 1. In this case, the scanning guide unit 28 guides the user to perform the scanning with the ultrasound probe 1 toward the target position and the target posture angle for imaging the recommended cross section R represented by the first arbitrary cross section image.

In a case in which it is determined that any one of the plurality of first rates of match is within a certain range of being greater than the first threshold value and equal to or less than the second threshold value, the cross section determination unit 58 determines that the recommended cross section R is present in the vicinity of the first arbitrary cross section image having the first matching degree, and transmits an instruction to the arbitrary cross section image generation unit 57 to cut out the plurality of second arbitrary cross section images from the three-dimensional ultrasound image T at the second positional interval and the second angular interval narrower than the first positional interval and the first angular interval in a case of cutting out the first arbitrary cross section image, to generate the plurality of second arbitrary cross section images in order to the arbitrary cross section image A having the matching degree exceeding the second threshold value. In this case, the arbitrary cross section image generation unit 57 cuts out the plurality of second arbitrary cross section images from a partial region of the three-dimensional ultrasound image T including the first arbitrary cross section image having a first matching degree that is greater than the first threshold value and equal to or less than the second threshold value, to generate the plurality of second arbitrary cross section images.

The cross section determination unit 58 compares a plurality of second rates of match with the second threshold value corresponding to the plurality of second arbitrary cross section images generated in this manner, to determine whether or not any one of the plurality of second arbitrary cross section images represents the recommended cross section R. In a case in which any one of the plurality of second rates of match exceeds the second threshold value, the cross section determination unit 58 determines that the second arbitrary cross section image having the second matching degree exceeding the second threshold value represents the recommended cross section R, and transmits an instruction to the scanning guide unit 28 to guide the user to perform the scanning with the ultrasound probe 1. In this case, the scanning guide unit 28 guides the user to perform the scanning with the ultrasound probe 1 toward the target position and the target posture angle for imaging the recommended cross section R represented by the second arbitrary cross section image.

In this way, in the region in which it is determined that the presence of the arbitrary cross section image A representing the recommended cross section R is suspected by the processing of the threshold value determination for the matching degree, the plurality of arbitrary cross section images A are generated with a narrower positional interval and angular interval, and the arbitrary cross section image A representing the recommended cross section R is determined based on the plurality of generated arbitrary cross section images A, so that the ultrasound diagnostic apparatus can guide the scanning at the target position and the target posture angle of the ultrasound probe 1, which can more accurately capture the recommended cross section R.

Next, an operation of the ultrasound diagnostic apparatus according to Embodiment 6 will be described with reference to the flowchart shown in FIG. 19. Hereinafter, a case will be described in which a specific organ is selected as the examination target of the subject, and the recommended cross section R corresponding to the selected organ is stored by the cross section determination unit 58.

Figure 12:
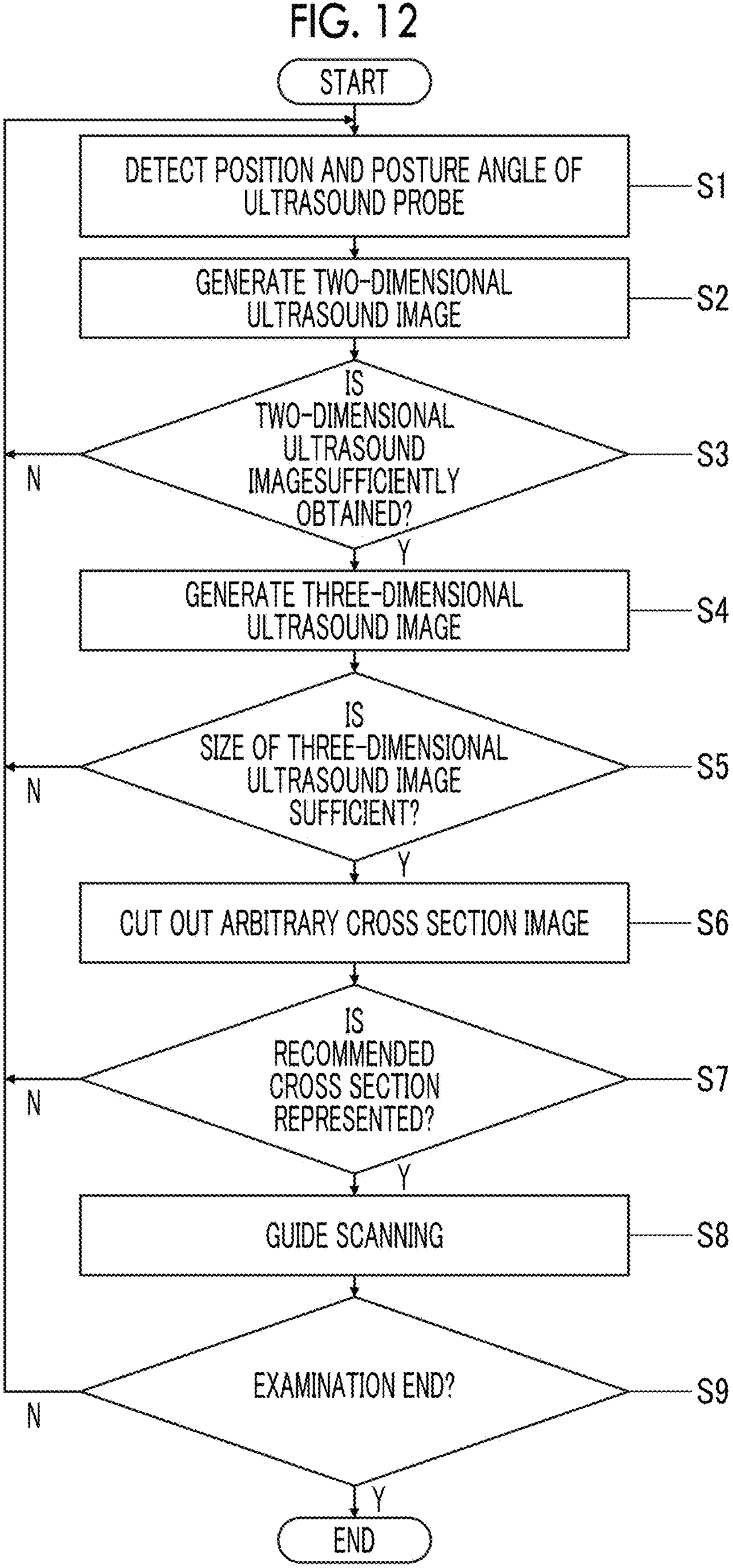
FIG. 12 is a flowchart showing an operation of the ultrasound diagnostic apparatus according to Embodiment 1 of the present invention.
Figure 19:
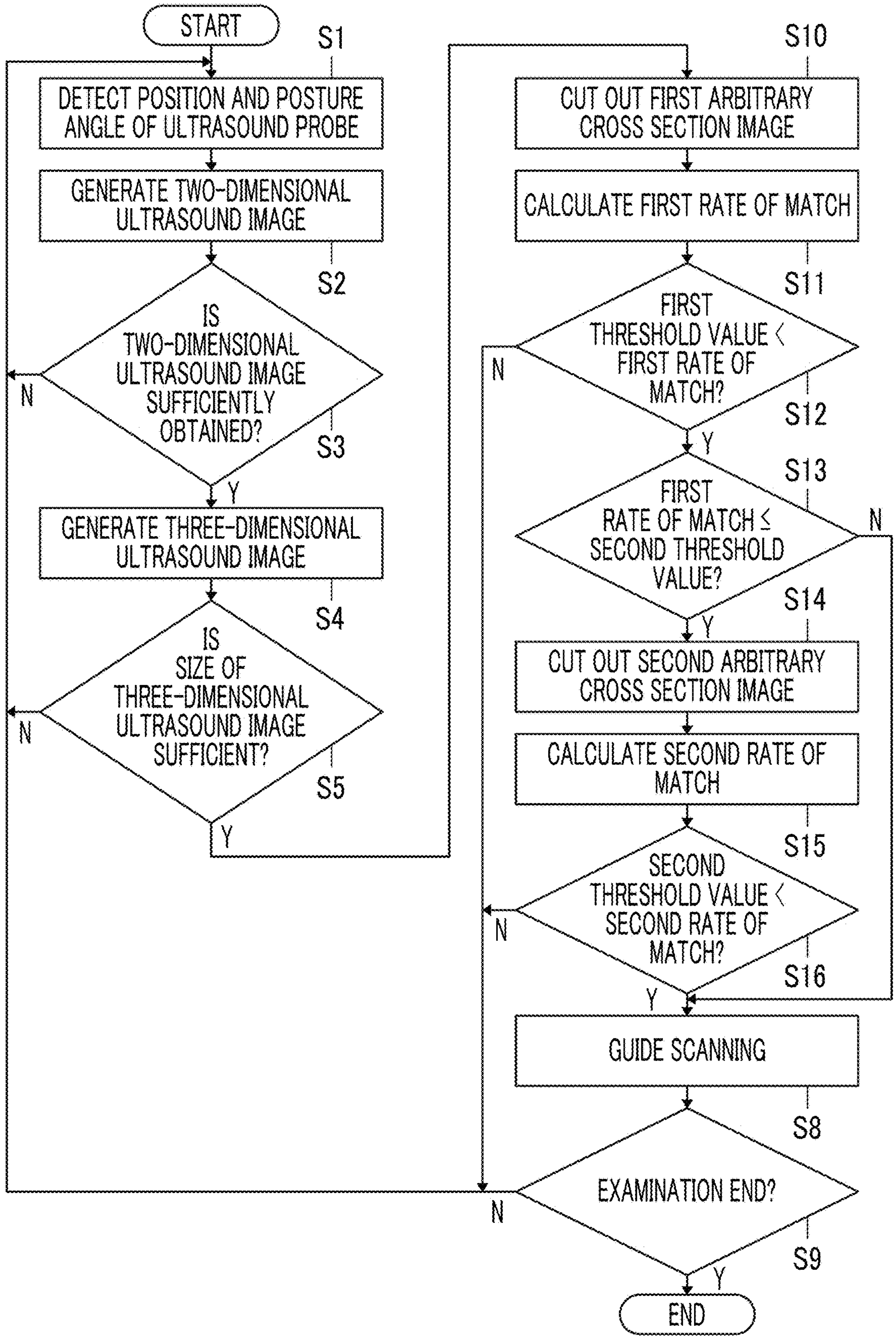
FIG. 19 is a flowchart showing an operation of the ultrasound diagnostic apparatus according to Embodiment 6 of the present invention.

In the flowchart shown in FIG. 19, the processing of step S6 and step S7 in the flowchart according to Embodiment 1 shown in FIG. 12 is replaced with the processing of step S10 to step S16. Steps S1 to S5, step S8, and step S9 in the flowcharts of FIGS. 12 and 19 are the same as each other, and thus detailed description of these steps will be omitted.

First, in step S1, the position and the posture angle of the ultrasound probe 1 are detected. Then, the two-dimensional ultrasound image U is generated in step S2, and it is determined in step S3 whether or not the two-dimensional ultrasound image U is sufficiently obtained. In a case in which it is determined in step S3 that the two-dimensional ultrasound image U is sufficiently obtained, the three-dimensional ultrasound image T is generated in step S4, and it is determined in step S5 whether or not the three-dimensional ultrasound image T has a sufficient size. In a case in which it is determined in step S5 that the three-dimensional ultrasound image T has a sufficient size, the processing proceeds to step S10.

In step S10, the arbitrary cross section image generation unit 57 cuts out the plurality of first arbitrary cross section images from the three-dimensional ultrasound image T generated in step S4 at the predetermined first positional interval and the predetermined first angular interval, to generate the plurality of first arbitrary cross section images.

In step S11, the cross section determination unit 58 calculates the first matching degree between the image pattern of the recommended cross section R and the image patterns of the plurality of first arbitrary cross section images generated in step S10.

In step S12, the cross section determination unit 58 determines whether or not the first matching degree corresponding to each of the plurality of first arbitrary cross section images calculated in step S11 is greater than the first threshold value. In a case in which it is determined in step S12 that all the first rates of match are equal to or less than the first threshold value, it is determined that the three-dimensional ultrasound image T generated in step S4 does not include the recommended cross section R, and the processing returns to step S1. In such a case, the processing of step S1 to step S12 is performed again.

In a case in which it is determined in step S12 that the first matching degree corresponding to any one of the plurality of first arbitrary cross section images is greater than the first threshold value, it is determined that the recommended cross section R is present in the vicinity of the cross section in the subject represented by the first arbitrary cross section image having the first matching degree, and the processing proceeds to step S13.

In step S13, the cross section determination unit 58 determines whether or not the first matching degree determined to be greater than the first threshold value in step S12 is equal to or less than the second threshold value. Here, in a case in which it is determined that the first matching degree is greater than the second threshold value, it is determined that the first arbitrary cross section image having the first matching degree represents the recommended cross section R, and the processing proceeds to step S8. In step S8, the scanning guide unit 28 guides the scanning toward the target position and the target posture angle of the ultrasound probe 1 for capturing the two-dimensional ultrasound image U corresponding to the first arbitrary cross section image determined to represent the recommended cross section R.

In step S13, in a case in which it is determined that the first matching degree determined to be greater than the first threshold value in step S12 is equal to or less than the second threshold value, it is determined that the recommended cross section R is present in the vicinity of the cross section in the subject represented by the first arbitrary cross section image having the first matching degree, and the processing proceeds to step S14.

In step S14, the arbitrary cross section image generation unit 57 cuts out the plurality of second arbitrary cross section images from the three-dimensional ultrasound image T generated in step S4 in the vicinity of the cross section represented by the first arbitrary cross section image having the matching degree that is greater than the first threshold value and equal to or less than the second threshold value determined in step S13 at the second positional interval narrower than the first positional interval and the second angular interval narrower than the first angular interval, to generate the plurality of second arbitrary cross section images.

In step 15, the cross section determination unit 58 calculates the second matching degree between each of the image patterns of the plurality of second arbitrary cross section images generated in step S14 and the image pattern of the recommended cross section R.

In step S16, the cross section determination unit 58 determines whether or not the second matching degree corresponding to each of the plurality of second arbitrary cross section images calculated in step S15 is greater than the second threshold value. In a case in which it is determined in step S16 that all the second rates of match are equal to or less than the second threshold value, it is determined that the second arbitrary cross section image representing the recommended cross section R cannot be specified, and the processing returns to step S1. In such a case, the processing of step S1 to step S15 is performed again.

In step S16, in a case in which it is determined that the second matching degree corresponding to any one of the plurality of second arbitrary cross section images calculated in step S15 is greater than the second threshold value, it is determined that the second arbitrary cross section image having the second matching degree represents the recommended cross section R, and the processing proceeds to step S8.

In following step S8, the scanning guide unit 28 guides the scanning toward the target position and the target posture angle of the ultrasound probe 1 for capturing the two-dimensional ultrasound image U corresponding to the second arbitrary cross section image determined to represent the recommended cross section R.

In step S9, the body controller 29E determines whether or not to end the examination of the subject. In a case in which it is determined to continue the examination in step S9, the processing returns to step S1, and the following steps are executed. In a case in which it is determined in step S9 to end the examination, the operation of the ultrasound diagnostic apparatus according to the flowchart of FIG. 19 is completed.

As described above, with the ultrasound diagnostic apparatus according to Embodiment 6, in a case in which the first matching degree corresponding to any one of the plurality of first arbitrary cross section images generated by the arbitrary cross section image generation unit 57 is greater than the first threshold value and equal to or less than the second threshold value, the plurality of second arbitrary cross section images are generated by the arbitrary cross section image generation unit 57, and in a case in which the second matching degree corresponding to the plurality of second arbitrary cross section images exceeds the second threshold value, the scanning guide unit 28 guides the scanning with the ultrasound probe 1. In this way, the plurality of second arbitrary cross section images are generated again at a narrower positional interval and angular interval in the vicinity of the first arbitrary cross section image having the first matching degree that is greater than the first threshold value and equal to or less than the second threshold value, and the determination is further performed by the cross section determination unit 58 by using the plurality of second arbitrary cross section images, so that the ultrasound diagnostic apparatus can guide the scanning at the target position and the target posture angle of the ultrasound probe 1 that can more accurately image the recommended cross section R.

It should be noted that ultrasound diagnostic apparatus according to Embodiment 6 has a configuration in which the arbitrary cross section image generation unit 26 and the cross section determination unit 27 in the ultrasound diagnostic apparatus according to Embodiment 1 are replaced with the arbitrary cross section image generation unit 57 and the cross section determination unit 58, but a configuration can also be adopted in which the arbitrary cross section image generation unit 26 and the cross section determination unit 27 in the ultrasound diagnostic apparatus according to Embodiments 2 to 5 are replaced with the arbitrary cross section image generation unit 57 and the cross section determination unit 58.

EXPLANATION OF REFERENCES

1, 1A: ultrasound probe
2, 2A, 2B, 2C, 2D, 2E: apparatus body
11: transducer array
12: transceiver circuit
13: position/posture sensor
21: two-dimensional ultrasound image generation unit
22: display controller
23: monitor
24: sensor information analysis unit
25: three-dimensional ultrasound image generation unit
26, 57: arbitrary cross section image generation unit
27, 58: cross section determination unit
28: scanning guide unit
29, 29A, 29B, 29C, 29D, 29E: body controller
30: input device
31: three-dimensional ultrasound image acquisition unit
32, 32A, 32B, 32C, 32D, 32E: processor
41: pulser
42: amplifying unit
43: AD conversion unit
44: beam former
45: signal processing unit
46: DSC
47: image processing unit
51: position/posture detection unit
52: image quality determination unit
53: image memory
54: examination target determination unit
55: scanning prompt unit
56: cross section specification information display unit
C: current cross section
A: arbitrary cross section image
J, M: message
R: recommended cross section
T: three-dimensional ultrasound image
U: two-dimensional ultrasound image
UT: typical two-dimensional ultrasound image

What is claimed is:

1. An ultrasound diagnostic apparatus comprising:
an ultrasound probe; and
a processor configured to:
detect a position and a posture angle of the ultrasound probe;
acquire a three-dimensional ultrasound image of an inside of a subject by transmitting and receiving an ultrasound beam by using the ultrasound probe with reference to the position and the posture angle of the ultrasound probe;
cut out a two-dimensional arbitrary cross section image from the three-dimensional ultrasound image, to generate the arbitrary cross section image;
compare an image pattern of a predetermined recommended cross section for a part of the subject with an image pattern of the arbitrary cross section image, to determine whether or not the arbitrary cross section image represents the recommended cross section; and
upon determining that the arbitrary cross section image represents the recommended cross section,
set a position and a posture angle of the ultrasound probe for capturing the arbitrary cross section image that is determined to represent the recommended cross section, as a target position and a target posture angle of the ultrasound probe for capturing a two-dimensional ultrasound image representing the recommended cross section, and
guide a user to perform scanning with the ultrasound probe toward the target position and the target posture angle of the ultrasound probe.

2. The ultrasound diagnostic apparatus according to claim 1,
wherein the processor is configured to:
calculate a matching degree between the image pattern of the recommended cross section and the image pattern of the arbitrary cross section image; and
determine that the arbitrary cross section image of which the matching degree exceeds a predetermined threshold value represents the recommended cross section.

3. The ultrasound diagnostic apparatus according to claim 1, further comprising:
a memory,
wherein the processor is configured to store the arbitrary cross section image determined to represent the recommended cross section in the memory.

4. The ultrasound diagnostic apparatus according to claim 2, further comprising:
a memory,
wherein the processor is configured to store the arbitrary cross section image determined to represent the recommended cross section in the memory.

5. The ultrasound diagnostic apparatus according to claim 3,
wherein the processor is configured to:
determine whether or not a quality of the arbitrary cross section image determined to represent the recommended cross section; and
store the arbitrary cross section image determined as that the quality is superior in the memory.

6. The ultrasound diagnostic apparatus according to claim 1,
wherein the processor is configured to, upon a predetermined time span is collapsed from starting scan of the ultrasound probe with keeping a state that the arbitrary cross section image is not determined to represent the recommended cross section, prompt the user to perform the scanning with the ultrasound probe.

7. The ultrasound diagnostic apparatus according to claim 2,
wherein the processor is configured to, upon a predetermined time span is collapsed from starting scan of the ultrasound probe with keeping a state that the arbitrary cross section image is not determined to represent the recommended cross section, prompt the user to perform the scanning with the ultrasound probe.

8. The ultrasound diagnostic apparatus according to claim 3, wherein the processor is configured to, upon a predetermined time span is collapsed from starting scan of the ultrasound probe with keeping a state that the arbitrary cross section image is not determined to represent the recommended cross section, prompt the user to perform the scanning with the ultrasound probe.

9. The ultrasound diagnostic apparatus according to claim 1, further comprising:

a monitor, wherein the processor is configured to display, on the monitor, a schema image in which the target position and the target posture angle of the ultrasound probe and a current position and a current posture angle of the ultrasound probe are superimposed.

10. The ultrasound diagnostic apparatus according to claim 2, further comprising:

a monitor, wherein the processor is configured to display, on the monitor, a schema image in which the target position and the target posture angle of the ultrasound probe and a current position and a current posture angle of the ultrasound probe are superimposed.

11. The ultrasound diagnostic apparatus according to claim 3, further comprising:

a monitor, wherein the processor is configured to display, on the monitor, a schema image in which the target position and the target posture angle of the ultrasound probe and a current position and a current posture angle of the ultrasound probe are superimposed.

12. The ultrasound diagnostic apparatus according to claim 1, further comprising:

a monitor, wherein the processor is configured to:

store a plurality of different recommended cross sections;

display, on the monitor, cross section specification information for specifying the recommended cross section determined to be represented by the arbitrary cross section image among the plurality of different recommended cross sections.

13. The ultrasound diagnostic apparatus according to claim 2, further comprising:

a monitor, wherein the processor is configured to:

store a plurality of different recommended cross sections;

display, on the monitor, cross section specification information for specifying the recommended cross section determined to be represented by the arbitrary cross section image among the plurality of different recommended cross sections.

14. The ultrasound diagnostic apparatus according to claim 1, wherein the processor is configured to:

store a plurality of different recommended cross sections; and set the recommended cross section that has been imaged among the plurality of different recommended cross sections, as a target not to be determined.

15. The ultrasound diagnostic apparatus according to claim 2, wherein the processor is configured to:

store a plurality of different recommended cross sections; and set the recommended cross section that has been imaged among the plurality of different recommended cross sections, as a target not to be determined.

16. The ultrasound diagnostic apparatus according to claim 1, wherein the processor is configured to:

store a plurality of different recommended cross sections and a target position and a target posture angle for imaging each of the plurality of different recommended cross sections; and upon determining that the arbitrary cross section image represents the recommended cross section that has already been imaged among the plurality of different recommended cross sections, guide the user to perform the scanning with the ultrasound probe toward the target position and the target posture angle of the ultrasound probe, which correspond to the recommended cross section that has not yet been imaged.

17. The ultrasound diagnostic apparatus according to claim 2, wherein the processor is configured to:

store a plurality of different recommended cross sections and a target position and a target posture angle for imaging each of the plurality of different recommended cross sections; and upon determining that the arbitrary cross section image represents the recommended cross section that has already been imaged among the plurality of different recommended cross sections, guide the user to perform the scanning with the ultrasound probe toward the target position and the target posture angle of the ultrasound probe, which correspond to the recommended cross section that has not yet been imaged.

18. The ultrasound diagnostic apparatus according to claim 1, wherein the processor is configured to:

store a plurality of different recommended cross sections, an indicator cross section different from the plurality of different recommended cross sections, and a correspondence relationship between target positions and target posture angles of the ultrasound probe for imaging the plurality of different recommended cross sections and a position and a posture angle of the ultrasound probe for imaging the indicator cross section;

calculate a matching degree between image patterns of the plurality of different recommended cross sections and the image pattern of the arbitrary cross section image and a matching degree between an image pattern of the indicator cross section and the image pattern of the arbitrary cross section image; and upon determining that the matching degree between the image pattern of the indicator cross section and the image pattern of the arbitrary cross section image exceeds a predetermined threshold value, guide the user to perform the scanning with the ultrasound probe toward a position and a posture angle of the ultrasound probe for capturing a two-dimensional ultrasound image representing the indicator cross section, and then guides the user to perform the scanning with the ultrasound probe toward the target position and the target posture angle corresponding to any one of the plurality of different recommended cross sections based on the correspondence relationship.

19. The ultrasound diagnostic apparatus according to claim 1, wherein the processor is configured to:

cut out a plurality of first arbitrary cross section images from the three-dimensional ultrasound image, at a predetermined first positional interval and a predetermined first angular interval, to generate the plurality of first arbitrary cross section images;

calculate a first matching degree between the image pattern of the recommended cross section and image patterns of the plurality of first arbitrary cross section images;

determine whether or not the first matching degree is greater than a predetermined first threshold value and equal to or less than a predetermined second threshold value;

upon determining that the first matching degree is greater than the first threshold value and equal to or less than the second threshold value, cut out a plurality of second arbitrary cross section images from a partial region of the three-dimensional ultrasound image including the first arbitrary cross section image corresponding to the first matching degree, at a second positional interval smaller than the first positional interval and a second angular interval smaller than the first angular interval, to generate the plurality of second arbitrary cross section images;

compare the image pattern of the recommended cross section with image patterns of the plurality of second arbitrary cross section images, to determine whether or not any one of the plurality of second arbitrary cross section images represents the recommended cross section; and further upon determining that any one of the plurality of second arbitrary cross section images represents the recommended cross section, guide the user to perform the scanning with the ultrasound probe toward the target position and the target posture angle of the ultrasound probe for capturing the two-dimensional ultrasound image representing the recommended cross section.

20. A method of controlling an ultrasound diagnostic apparatus, the method comprising:

detecting a position and a posture angle of an ultrasound probe;

generating a plurality of two-dimensional ultrasound images of an inside of a subject by transmitting and receiving an ultrasound beam by using the ultrasound probe with reference to the position and the posture angle of the ultrasound probe, which are detected;

generating a three-dimensional ultrasound image of the inside of the subject based on the position and the posture angle of the ultrasound probe, which are detected, and the plurality of two-dimensional ultrasound images;

cutting out a two-dimensional arbitrary cross section image from the three-dimensional ultrasound image, to generate the arbitrary cross section image;

comparing an image pattern of a predetermined recommended cross section for a part of the subject with an image pattern of the arbitrary cross section image, to determine whether or not the arbitrary cross section image represents the recommended cross section; and upon determining that the arbitrary cross section image represents the recommended cross section, setting a position and a posture angle of the ultrasound probe for capturing the arbitrary cross section image that is determined to represent the recommended cross section, as a target position and a target posture angle of the ultrasound probe for capturing a two-dimensional ultrasound image representing the recommended cross section, and guiding a user to perform scanning with the ultrasound probe toward the target position and the target posture angle of the ultrasound probe.

* * * * *